(12) United States Patent
Lee et al.

(10) Patent No.: US 6,459,758 B1
(45) Date of Patent: Oct. 1, 2002

(54) METHOD AND APPARATUS FOR DISCRETE TOMOGRAPHY

(75) Inventors: David Lee, Warren; Yehuda Vardi, Watchung, both of NJ (US)

(73) Assignee: Lucent Technologies Inc., Murray Hill, NJ (US)

( * ) Notice: Subject to any disclaimer, the term of this patent is extended or adjusted under 35 U.S.C. 154(b) by 0 days.

(21) Appl. No.: 09/137,533

(22) Filed: Aug. 21, 1998

Related U.S. Application Data

(60) Provisional application No. 60/056,931, filed on Aug. 22, 1997.

(51) Int. Cl.[7] .......................... G01N 23/04; G01N 23/08
(52) U.S. Cl. ............................................ 378/22; 250/311
(58) Field of Search ................................ 250/310, 311; 378/21, 22

(56) References Cited

U.S. PATENT DOCUMENTS 6,051,834 A * 4/2000 Kakibayashi et al. ....... 250/311

* cited by examiner

*Primary Examiner*—David V. Bruce

(57) ABSTRACT

Discrete tomographic apparatus comprises an electron microscope for irradiating a sample comprising an atomic lattice structure. Line count data is obtained for the main directions of a cross section of the sample. A non-linear programming algorithm is applied to obtain probabilities of occupancy of lattice sites by atoms of the sample. The non-linear programming algorithm comprises an iterative application of the expectation/maximization algorithm upper bounded by the constraint that each variable is valued at less than or equal to one. Once the algorithm is iteratively applied a phantom image of the cross section of the sample is generated. The cross sectional area may be less than one thousand atoms by one thousand atoms.

16 Claims, 32 Drawing Sheets

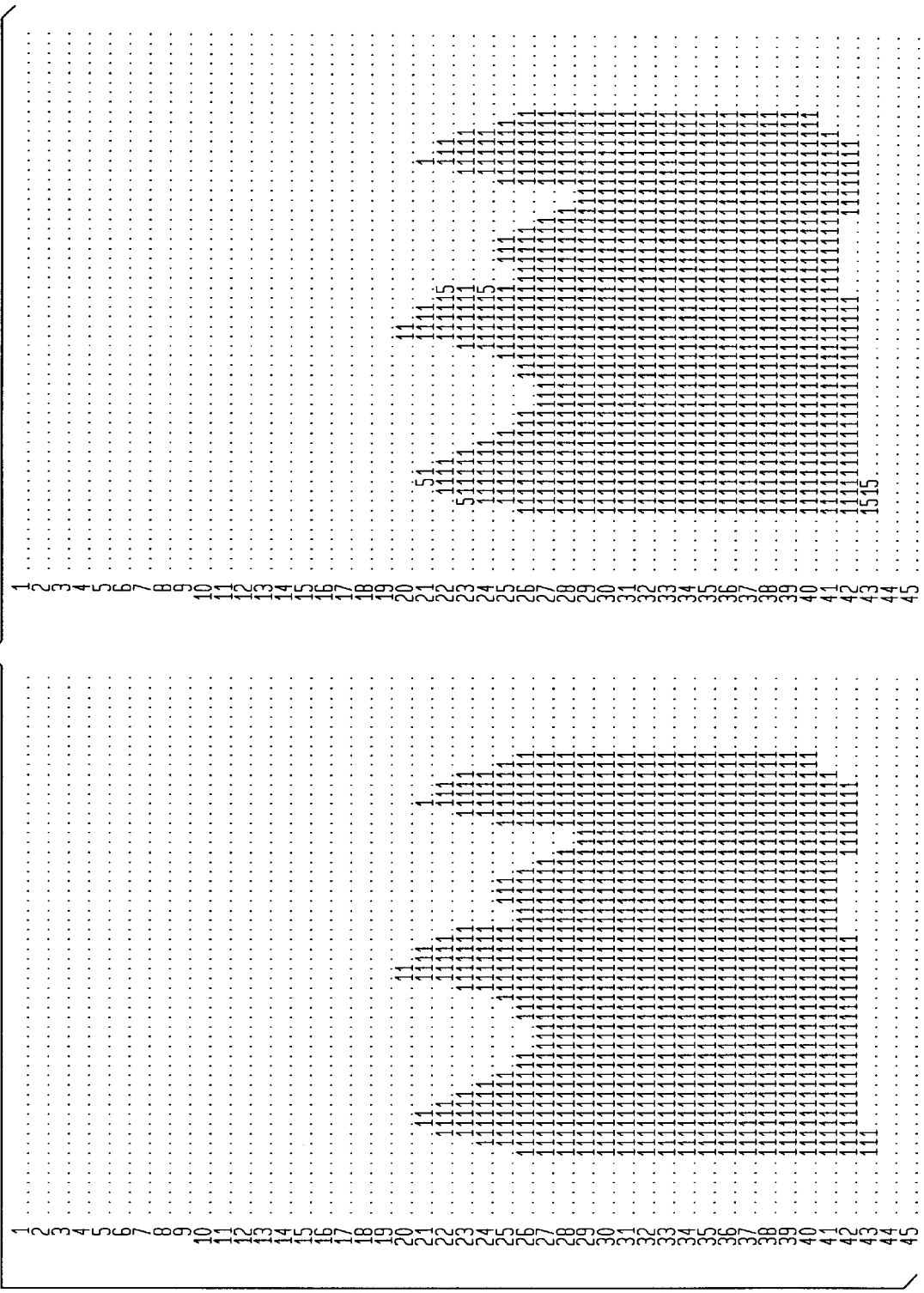
FIG. 1.1

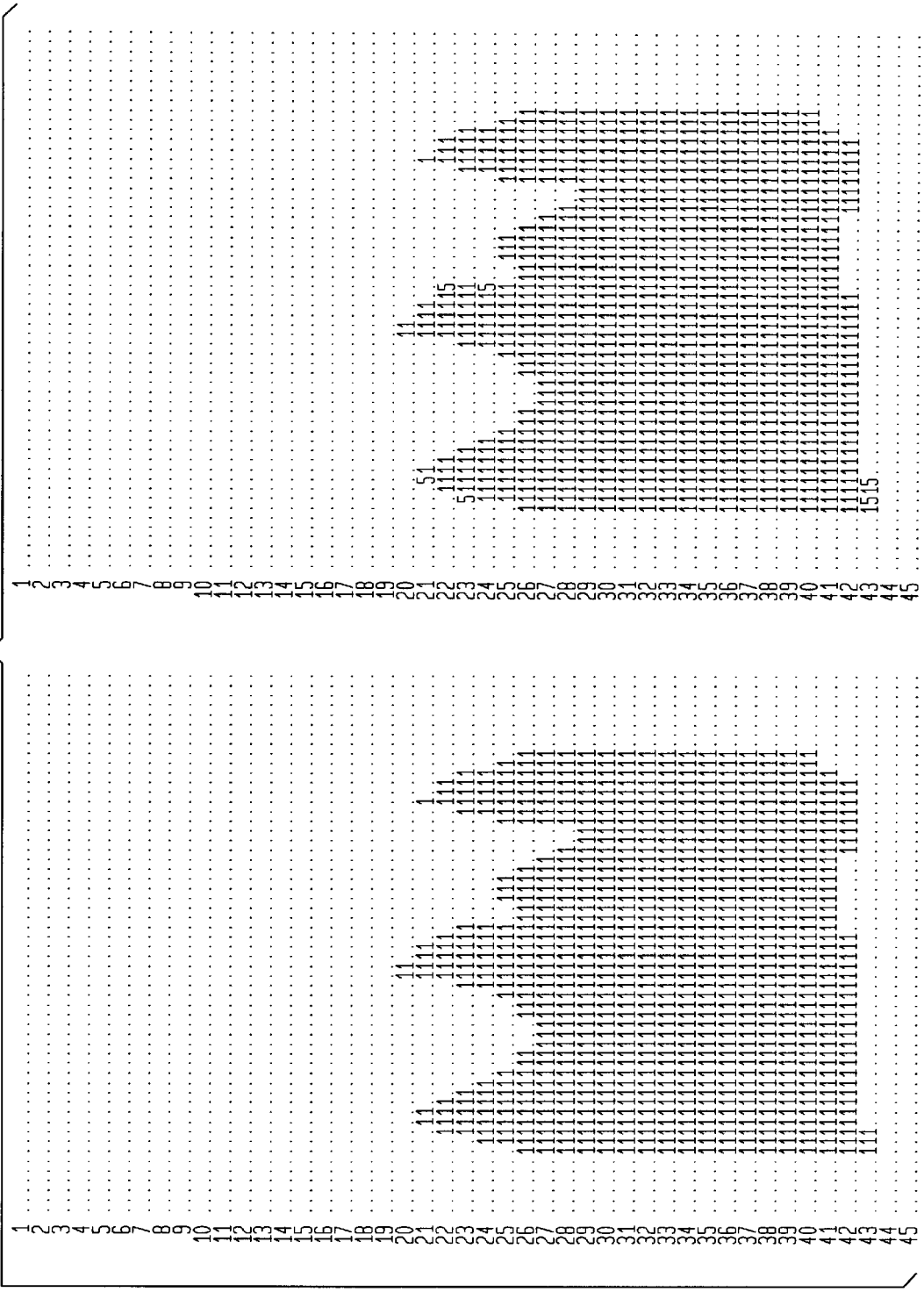
FIG. 1.2

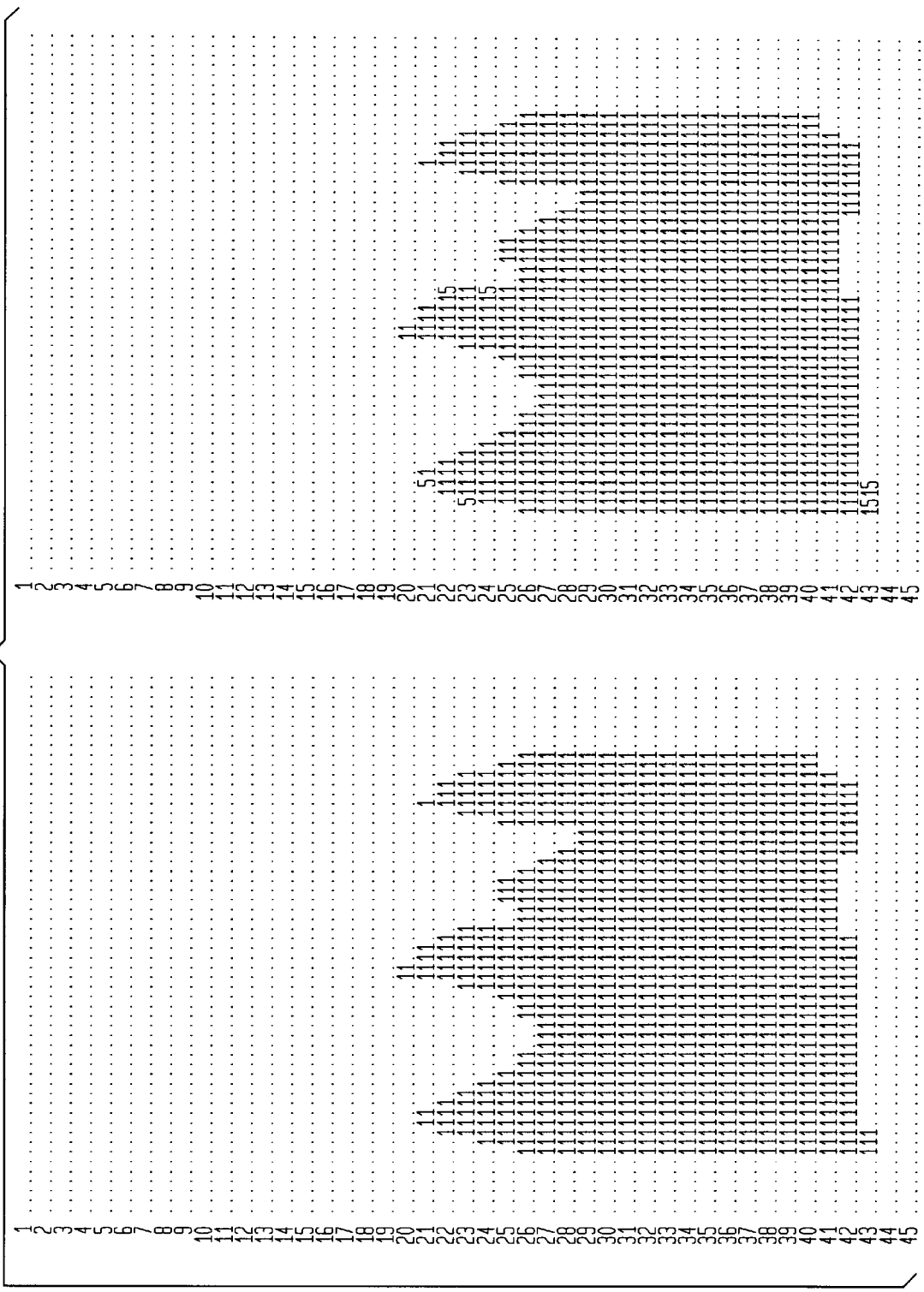
FIG. 1.3

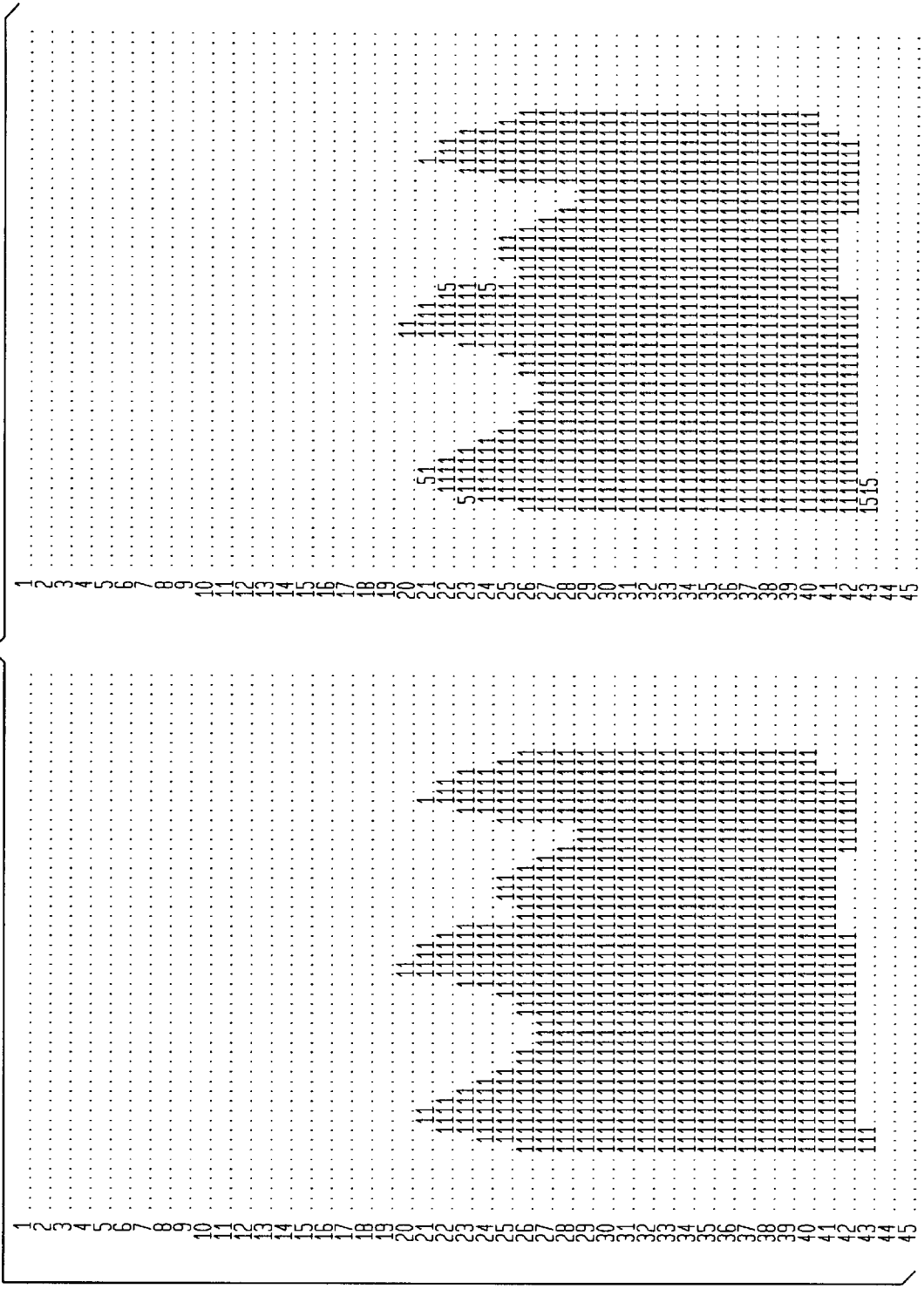
FIG. 1.4

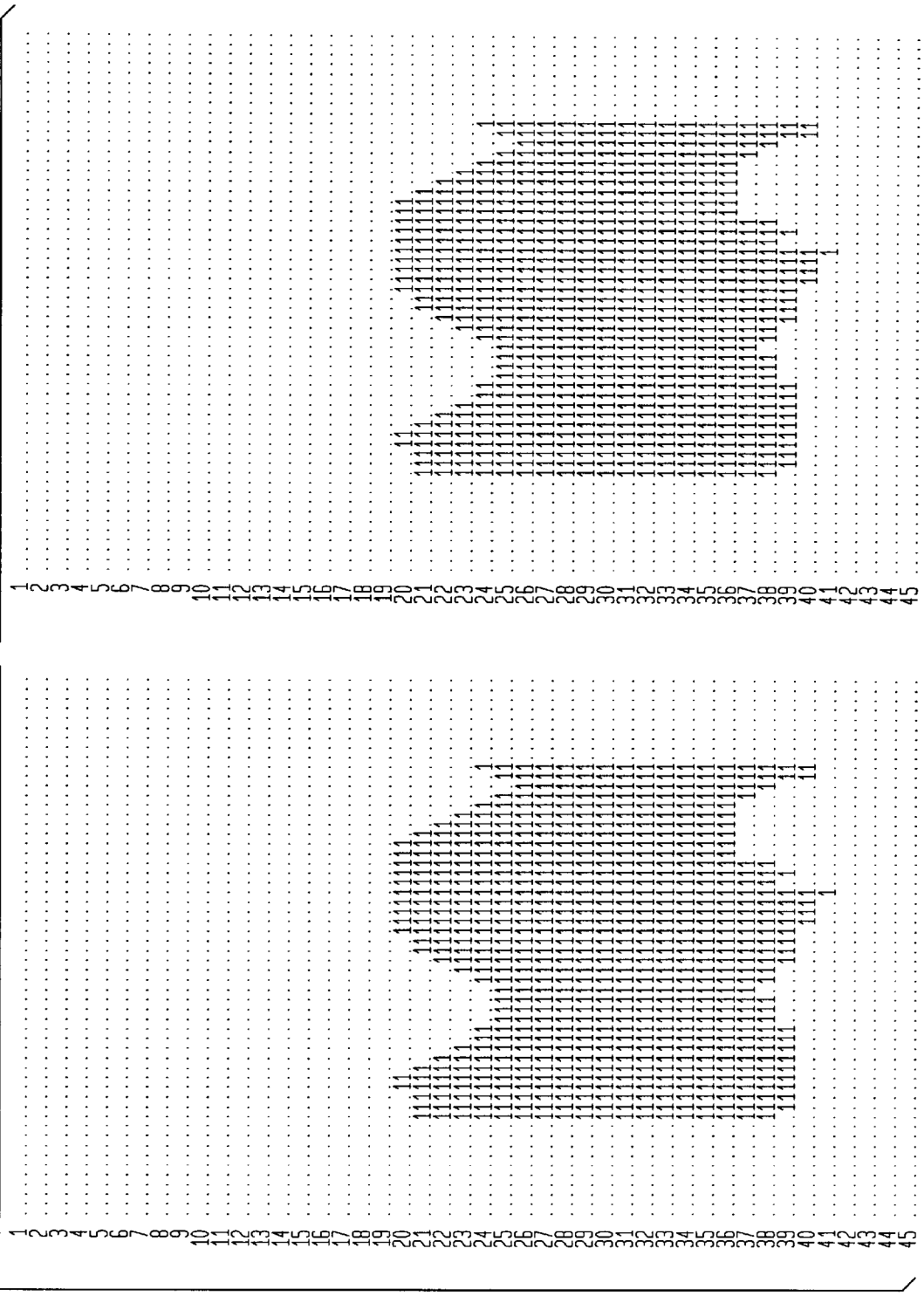
FIG. 2.1

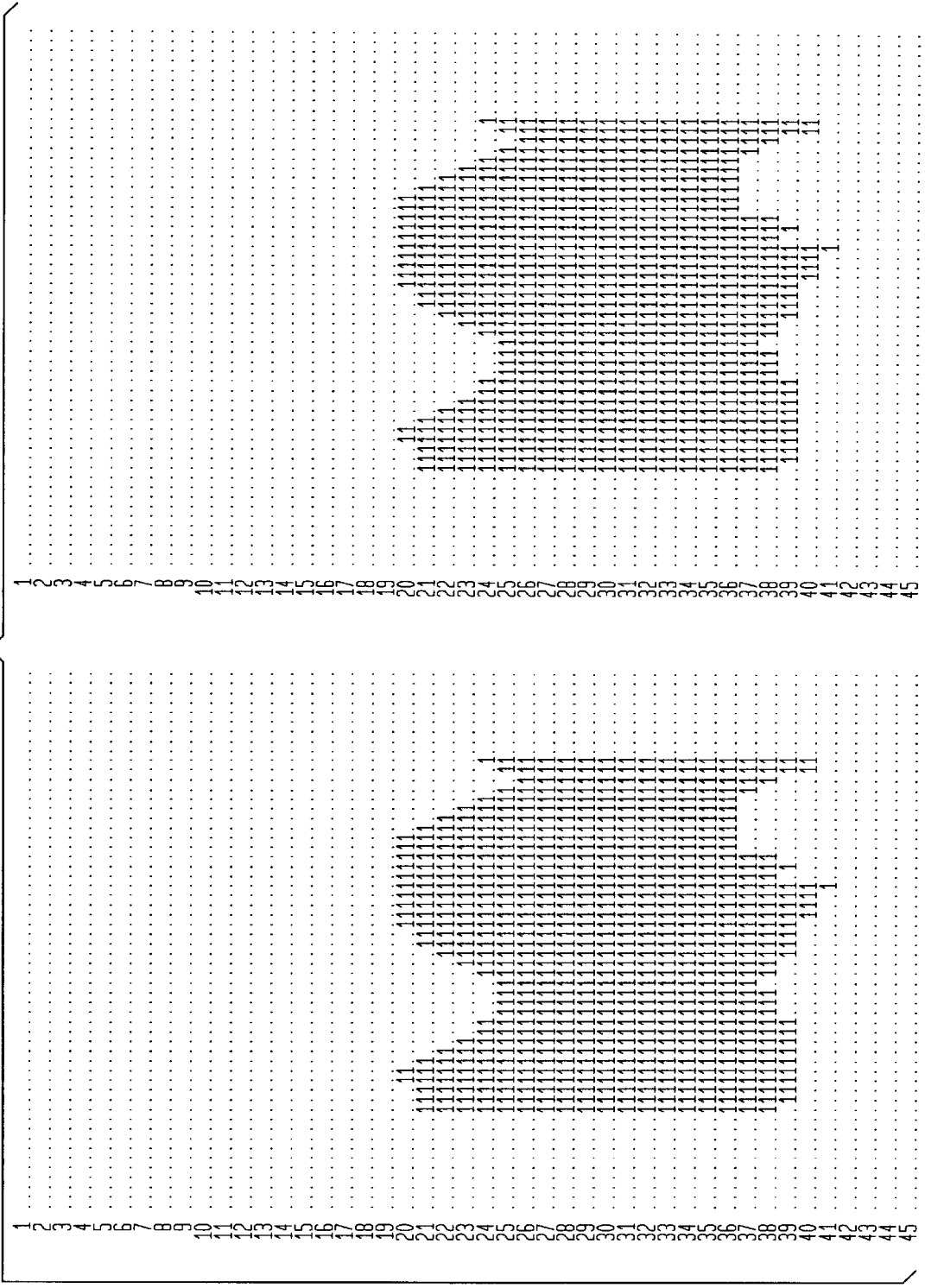
FIG. 2.2

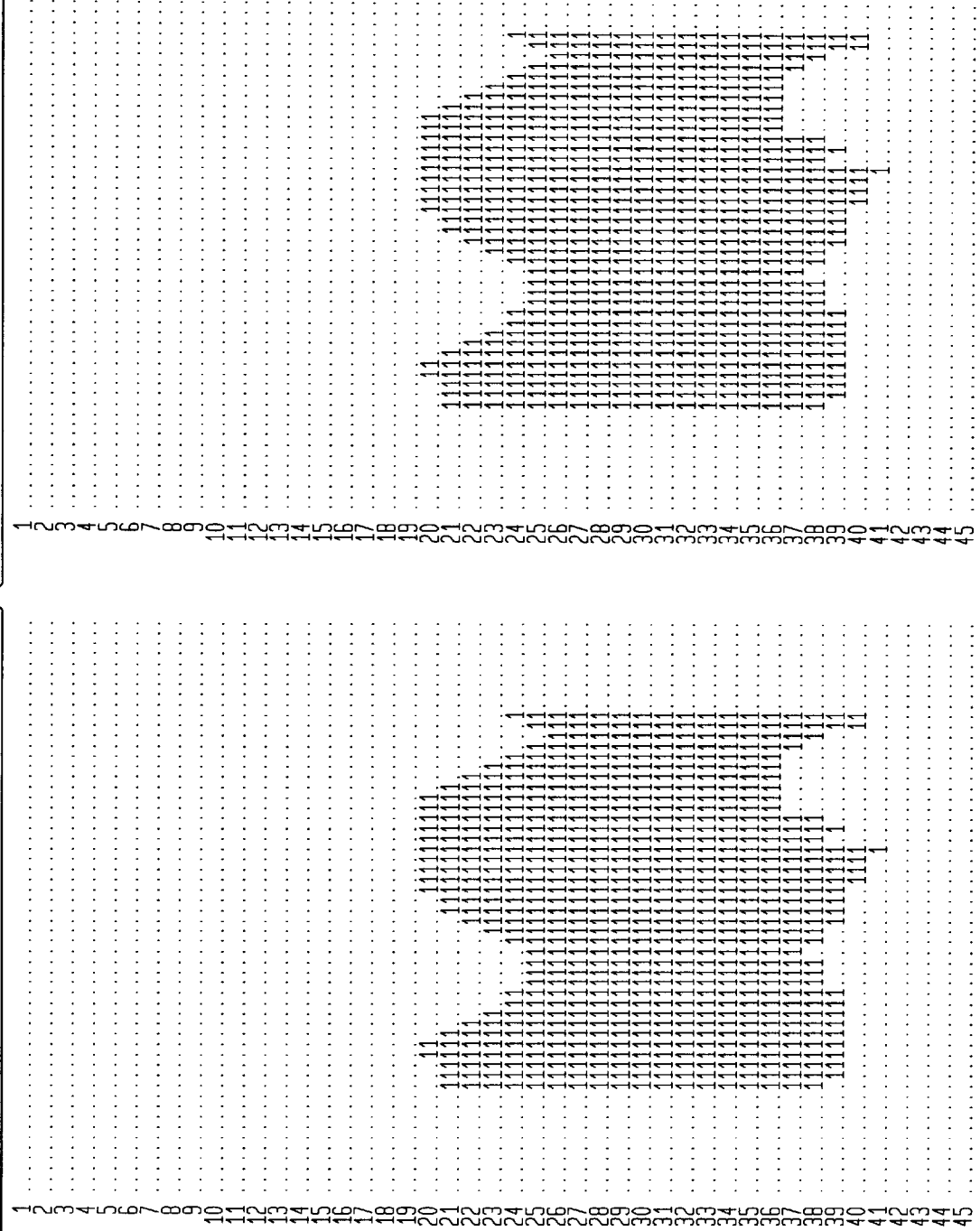
FIG. 2.3

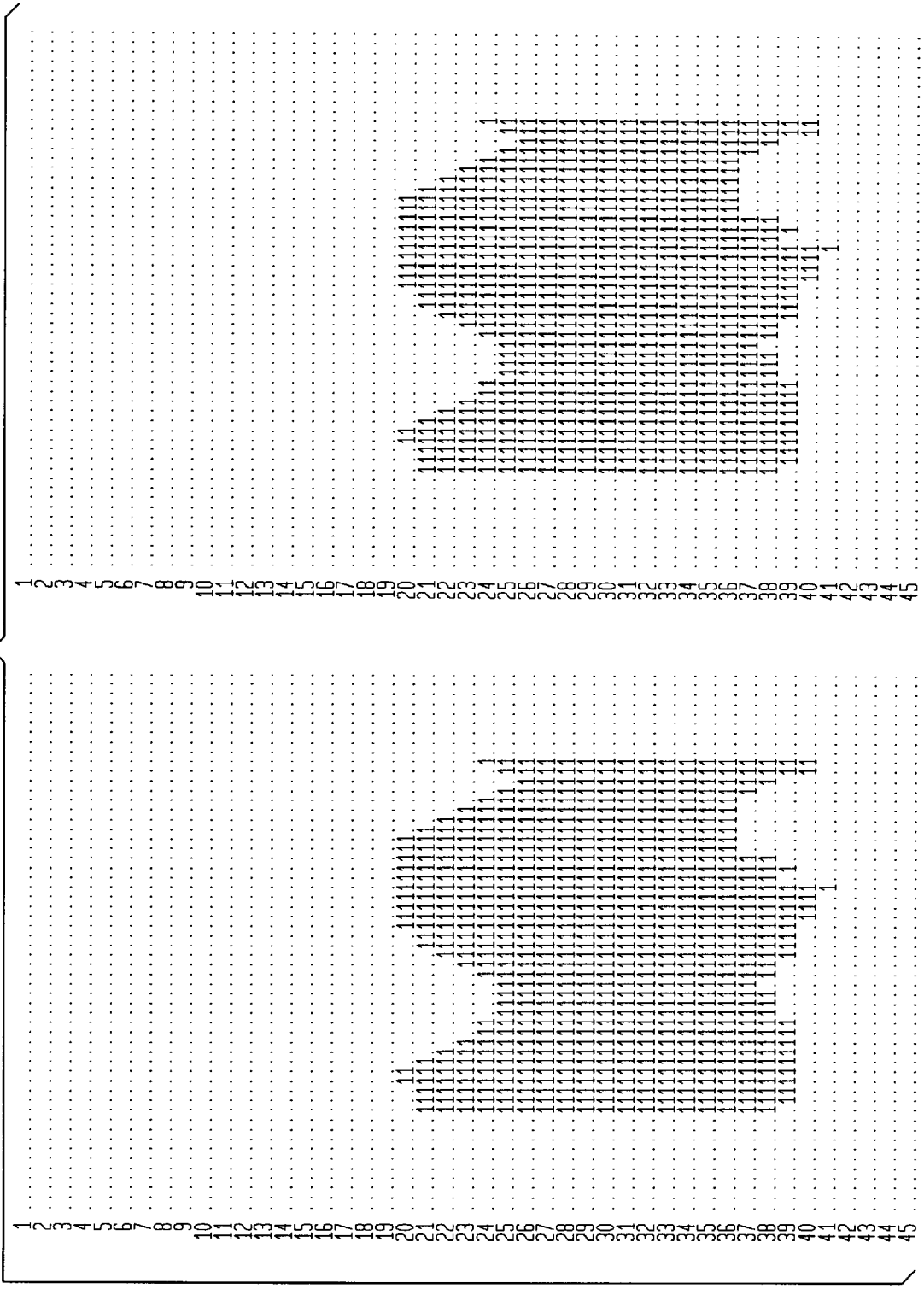

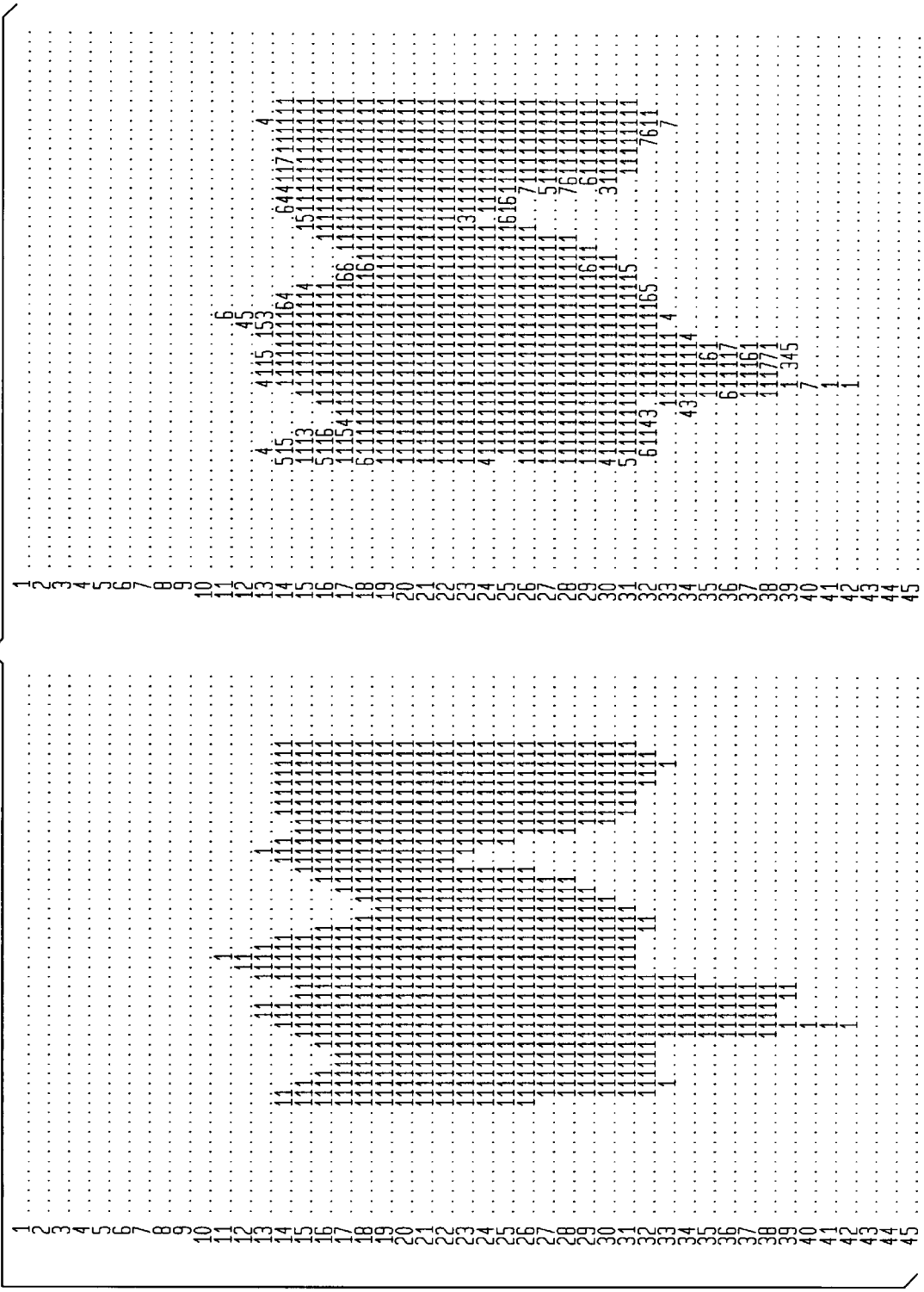
FIG. 3.2

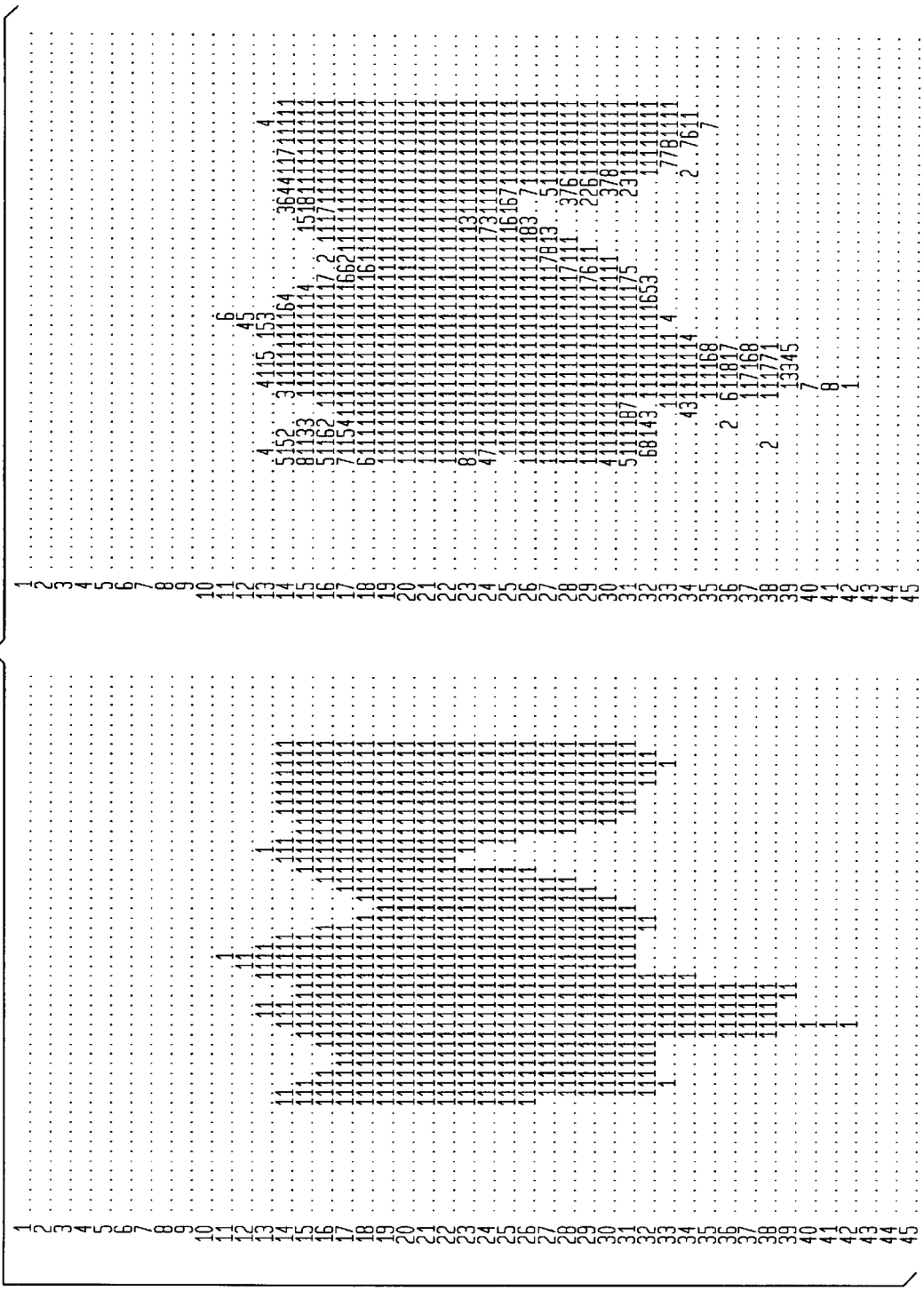
FIG. 3.2

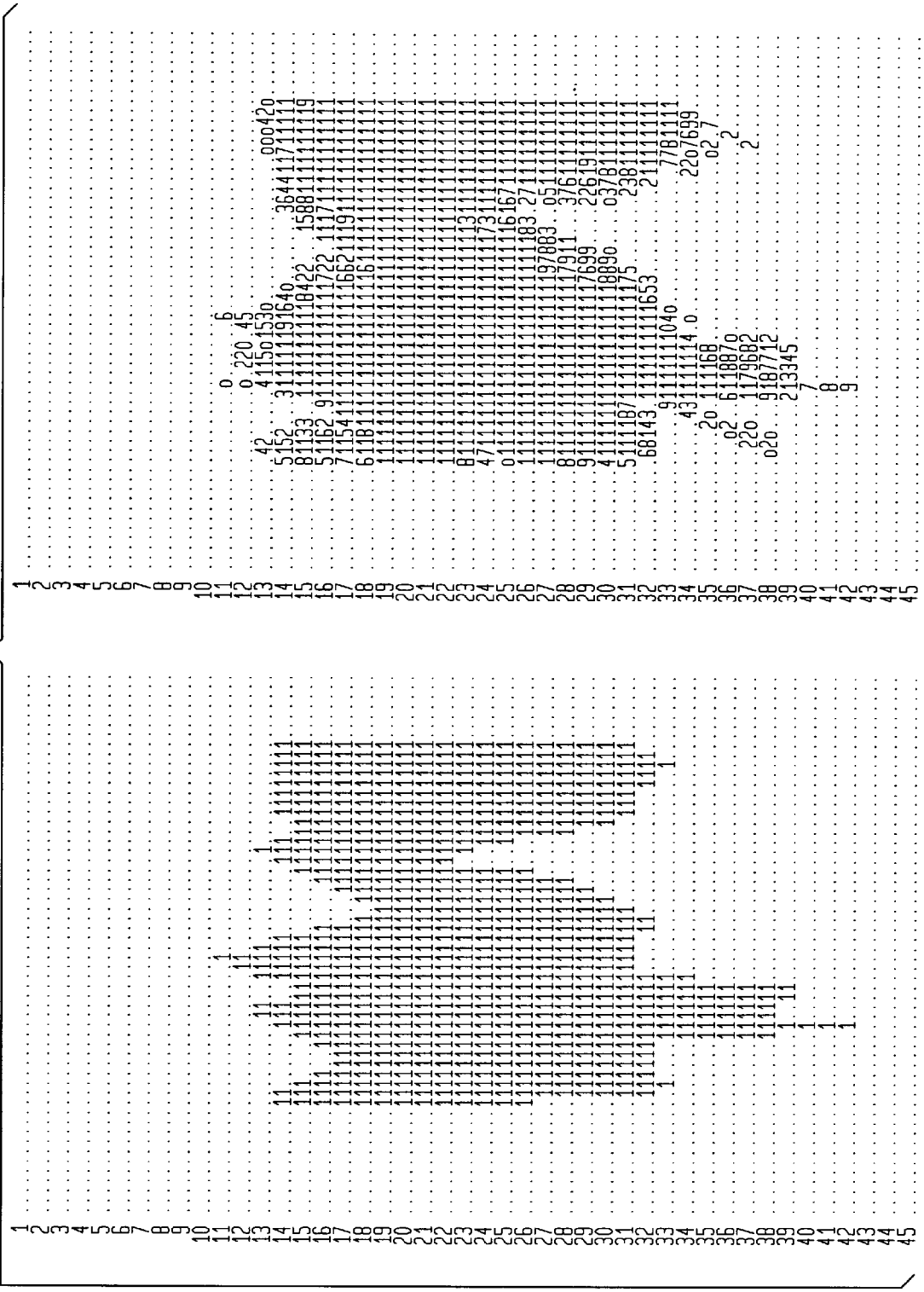
FIG. 3.4

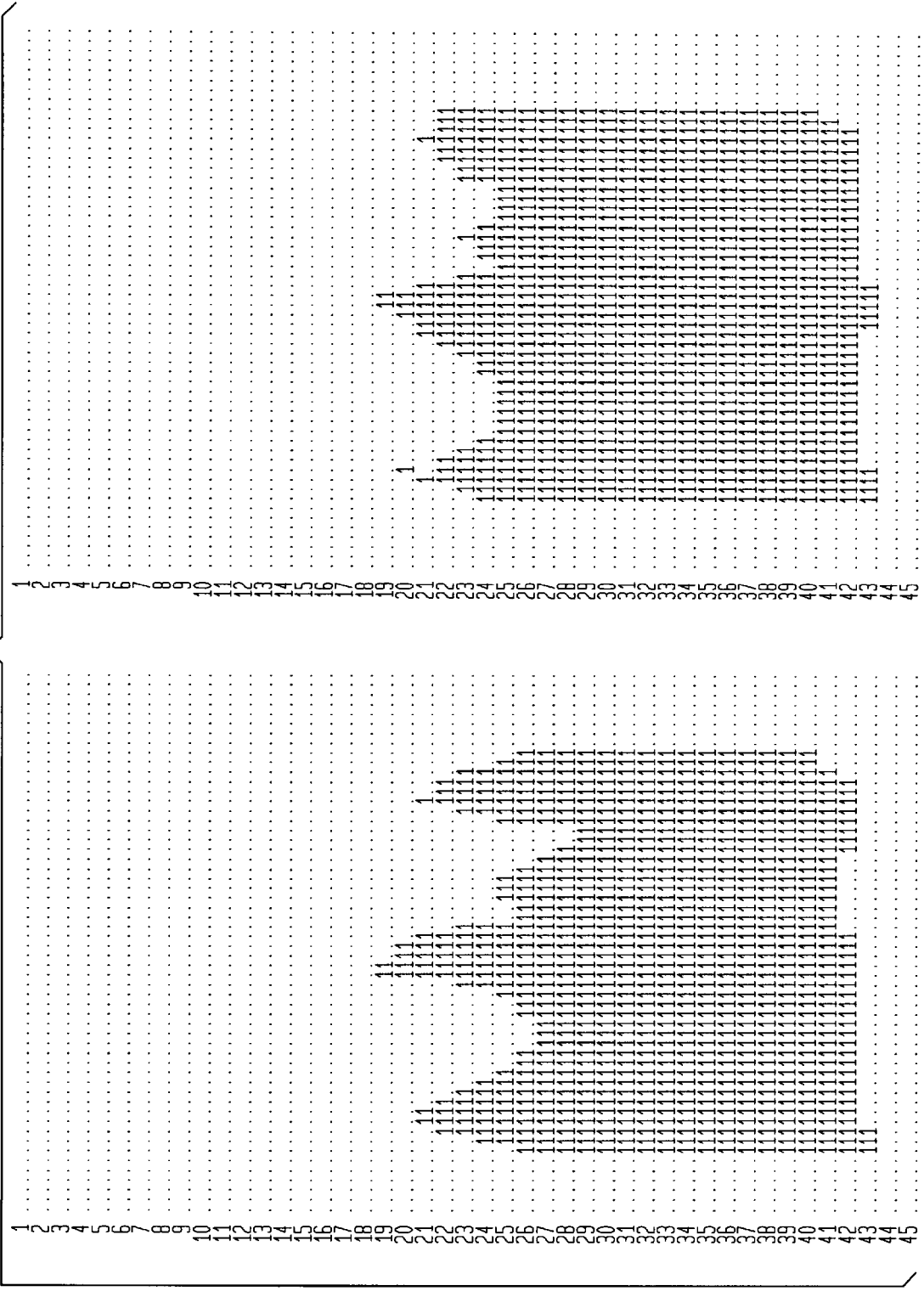
FIG. 4.1

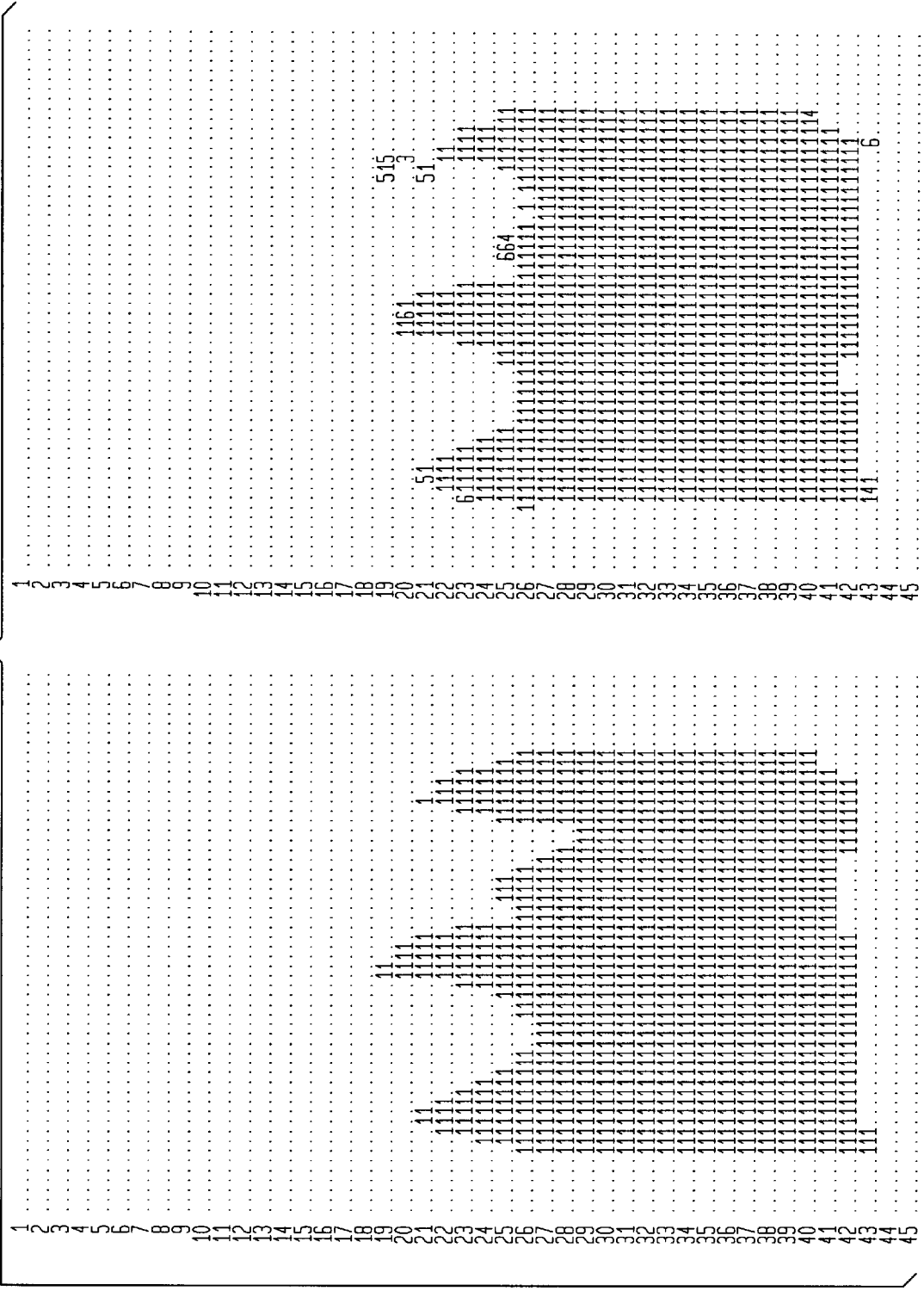

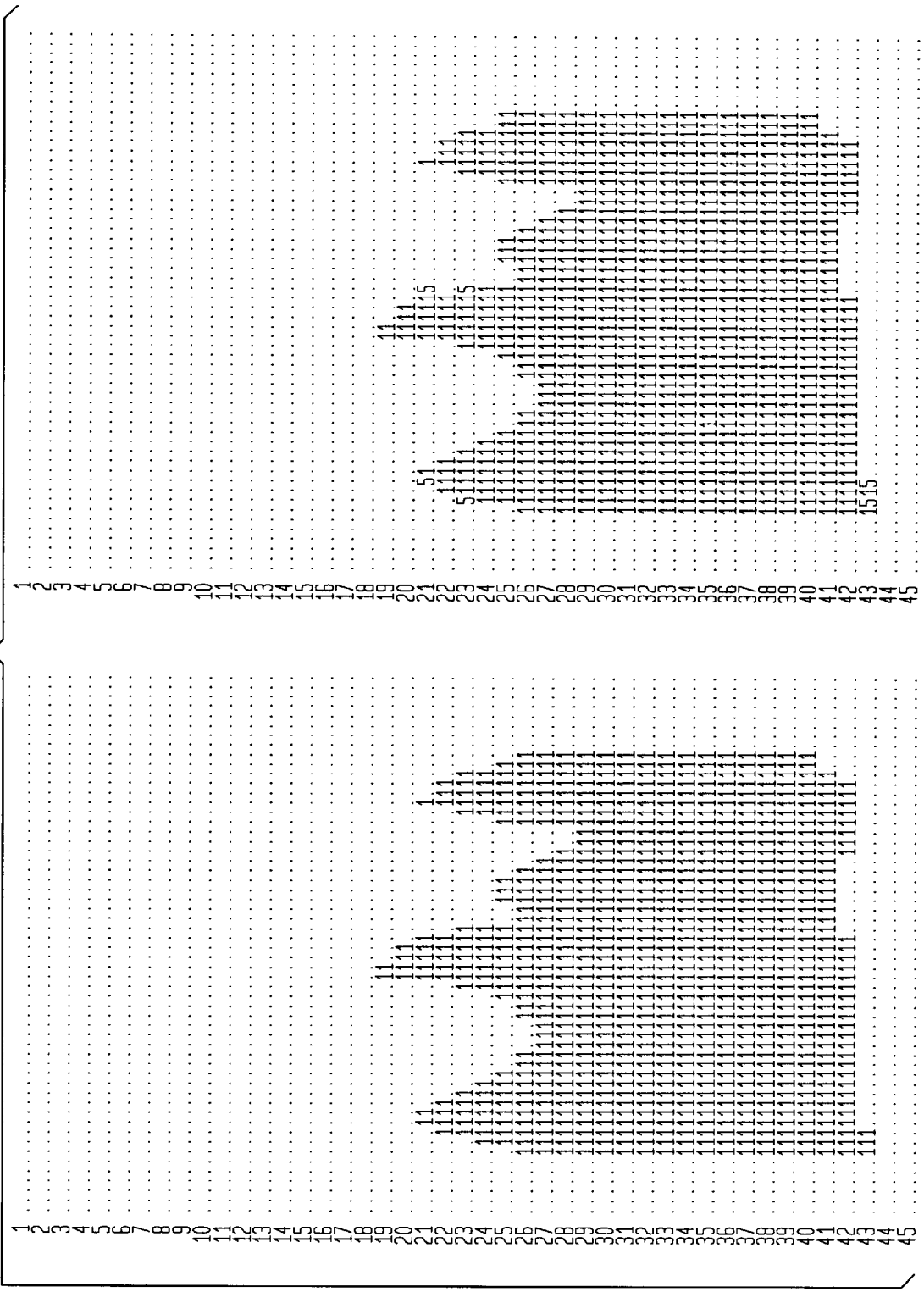

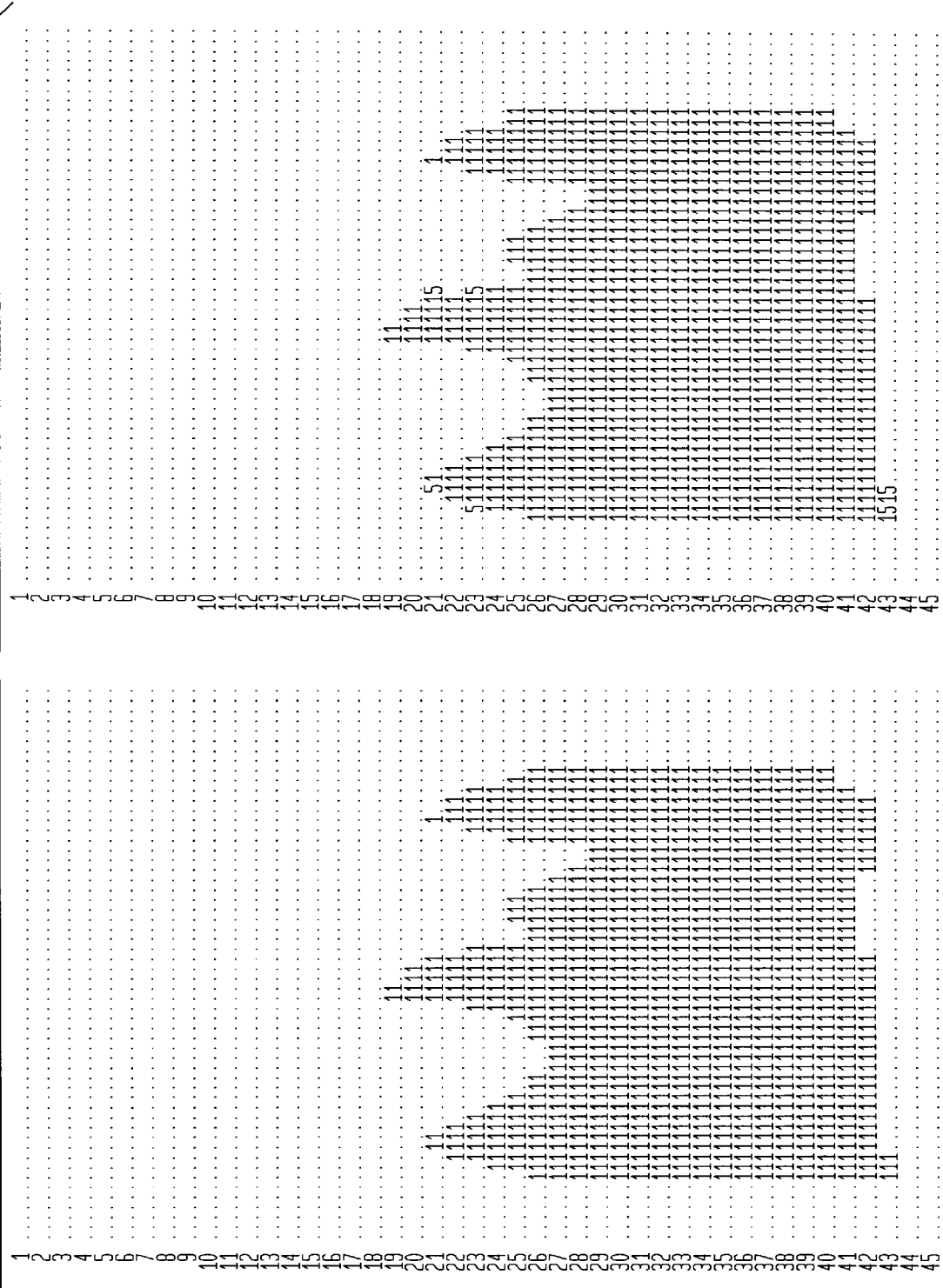
FIG. 4.4

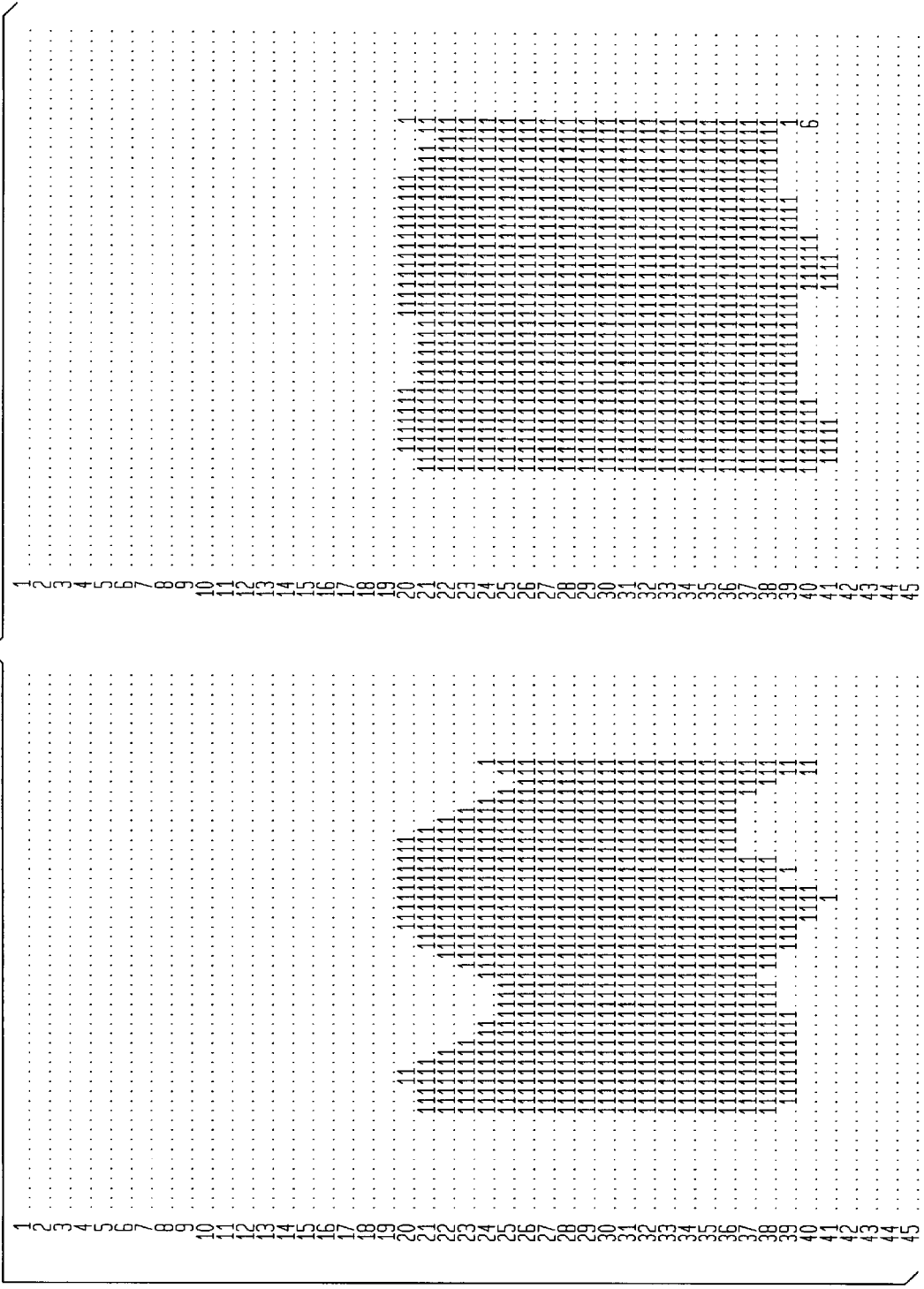

FIG. 5.2

FIG. 5.3

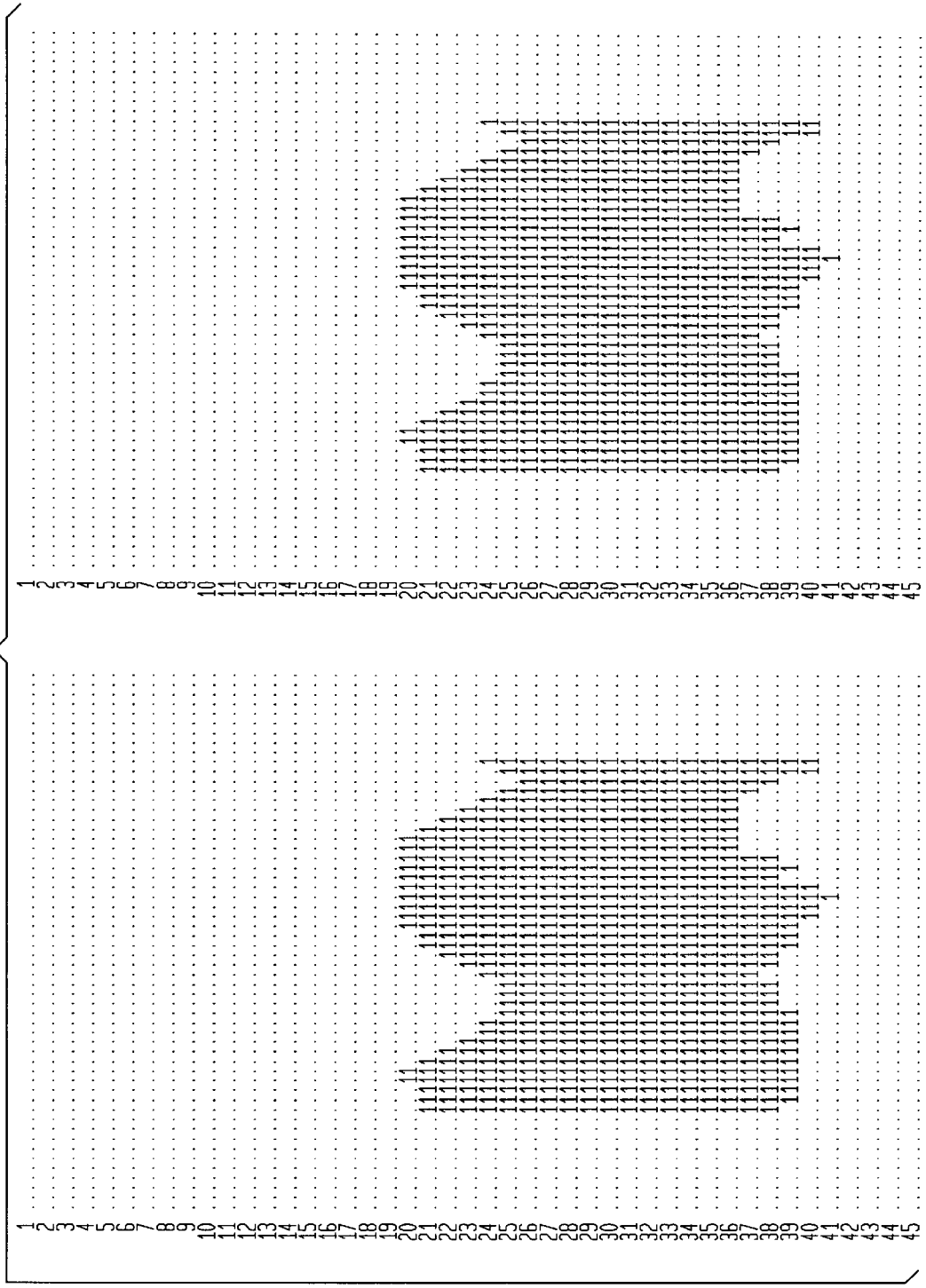

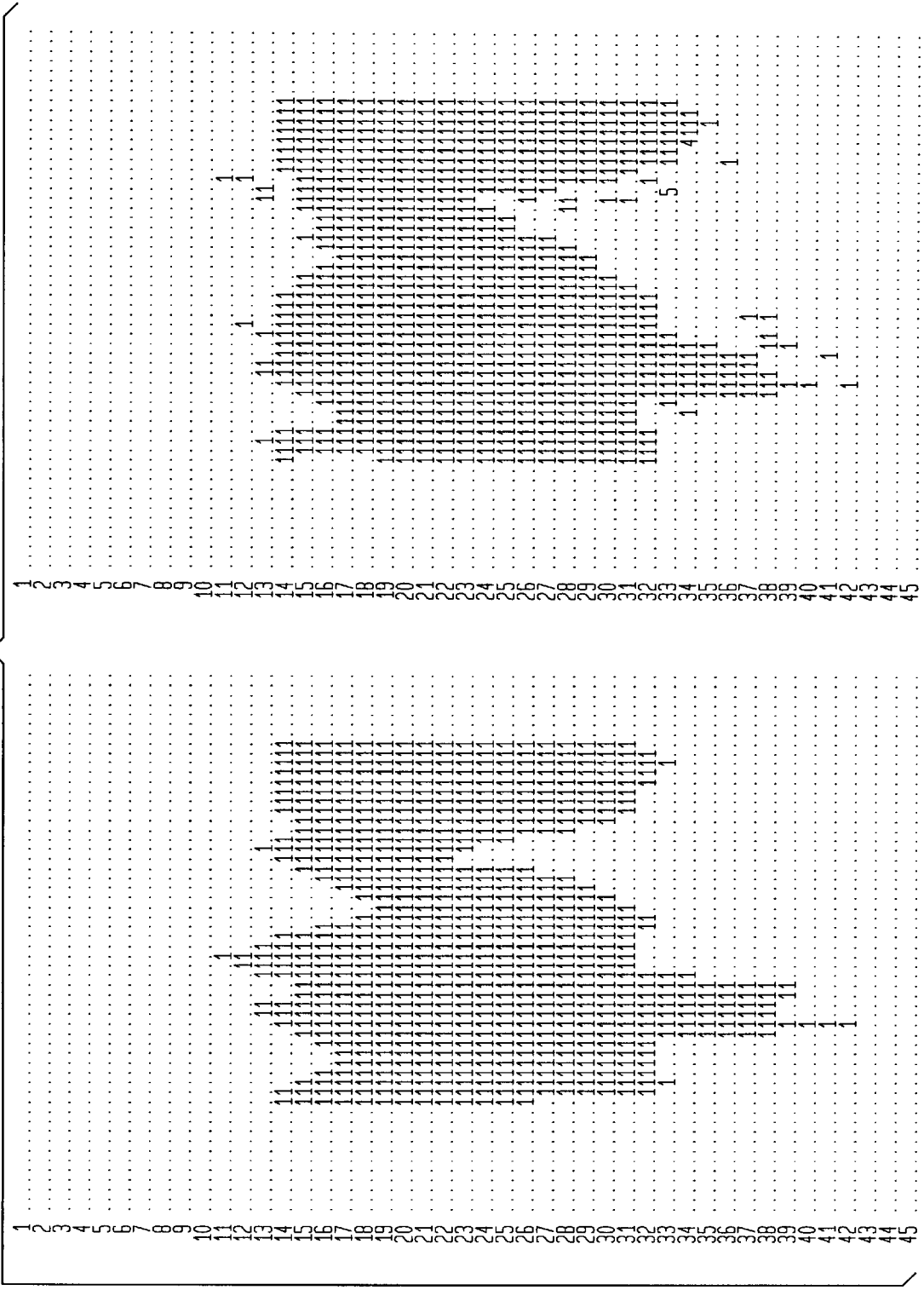
FIG. 6.1

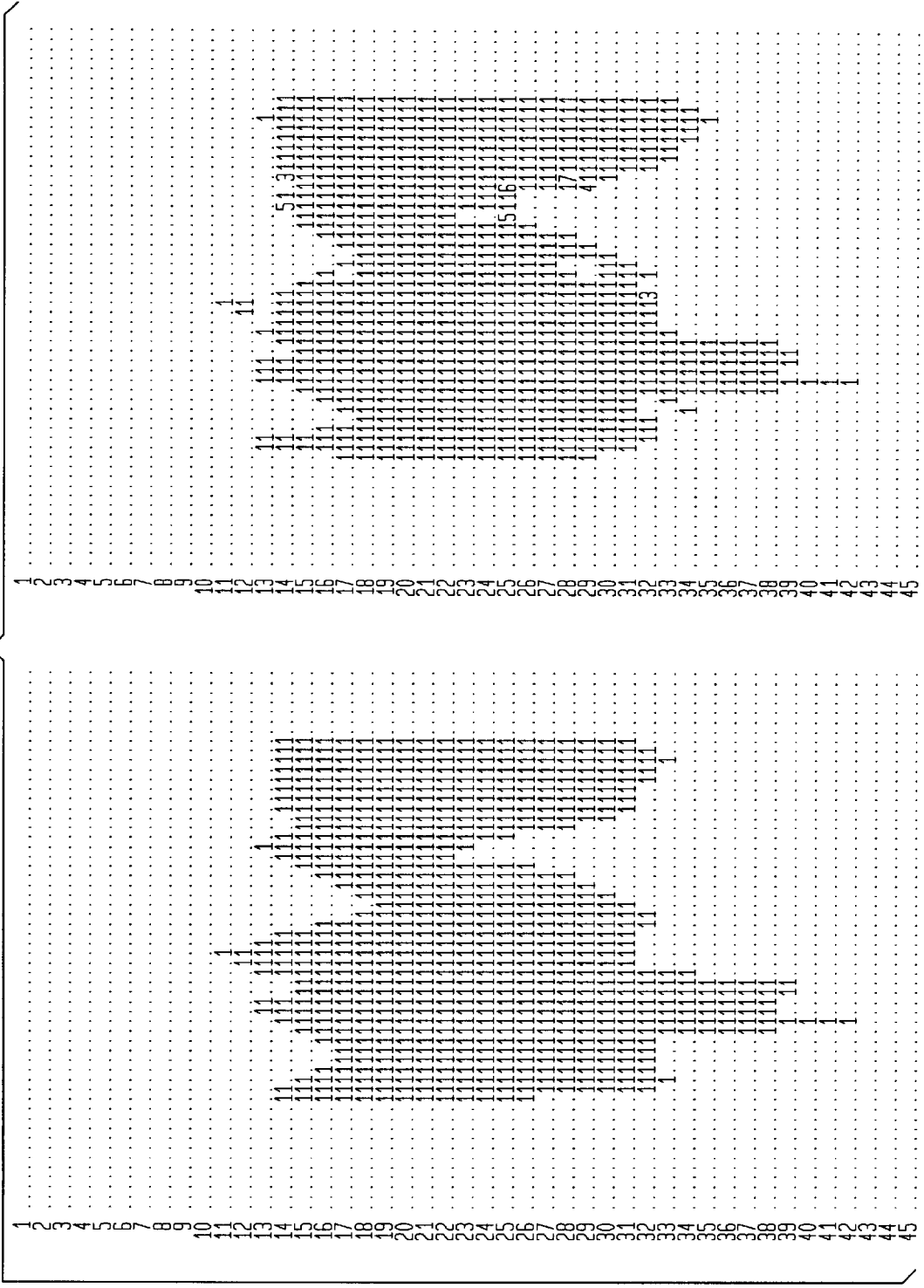
FIG. 6.2

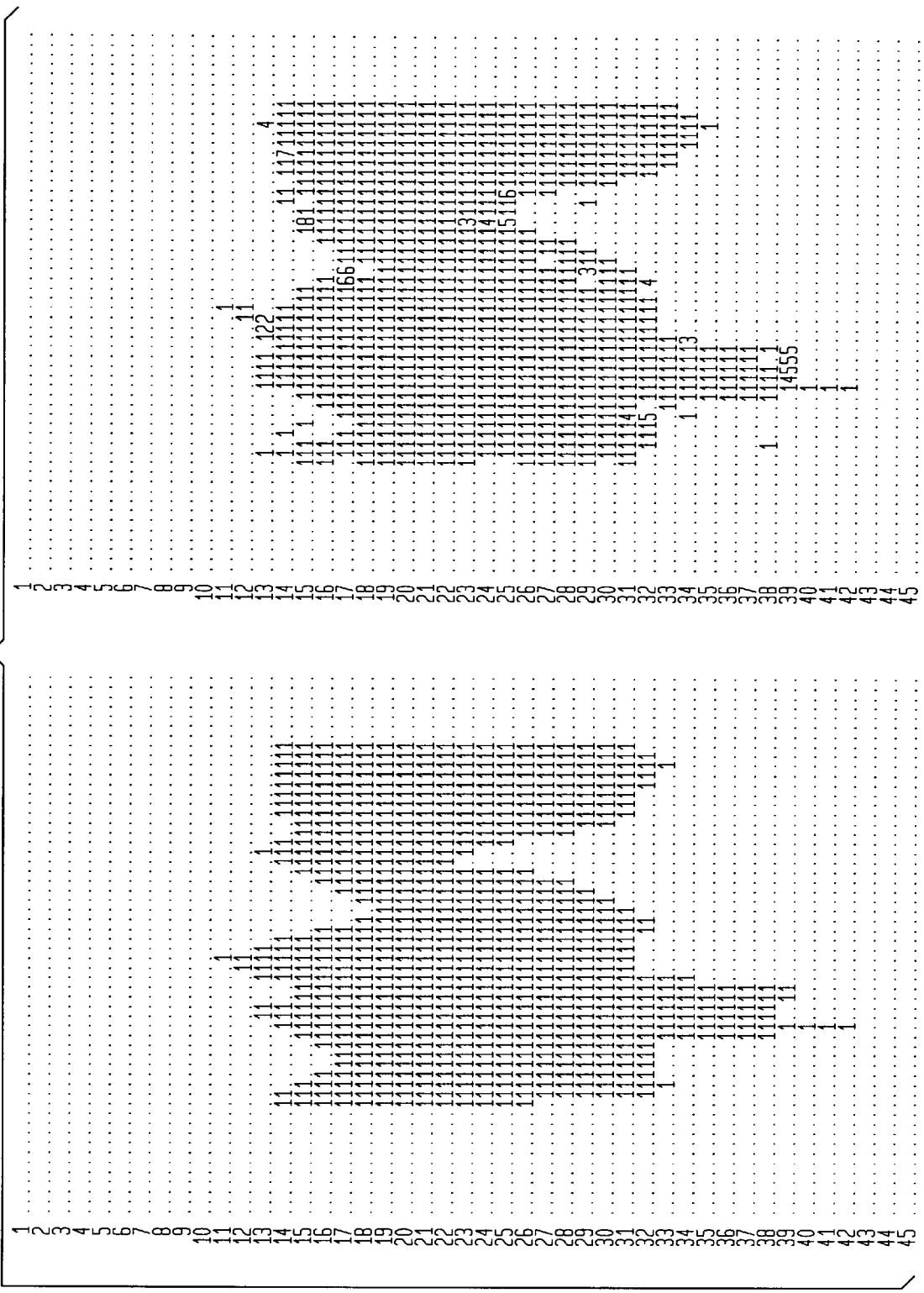
FIG. 6.3

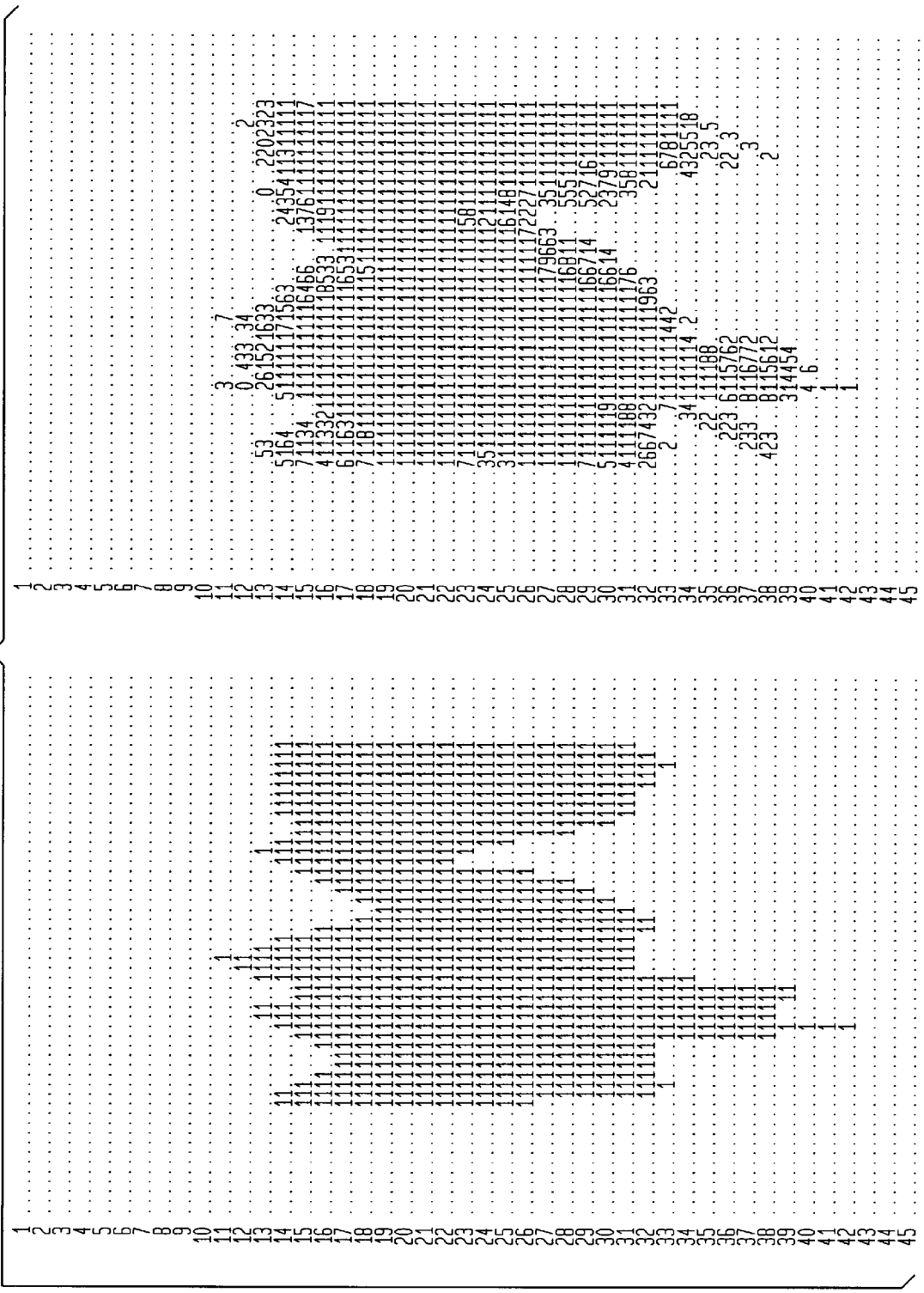
FIG. 6.4

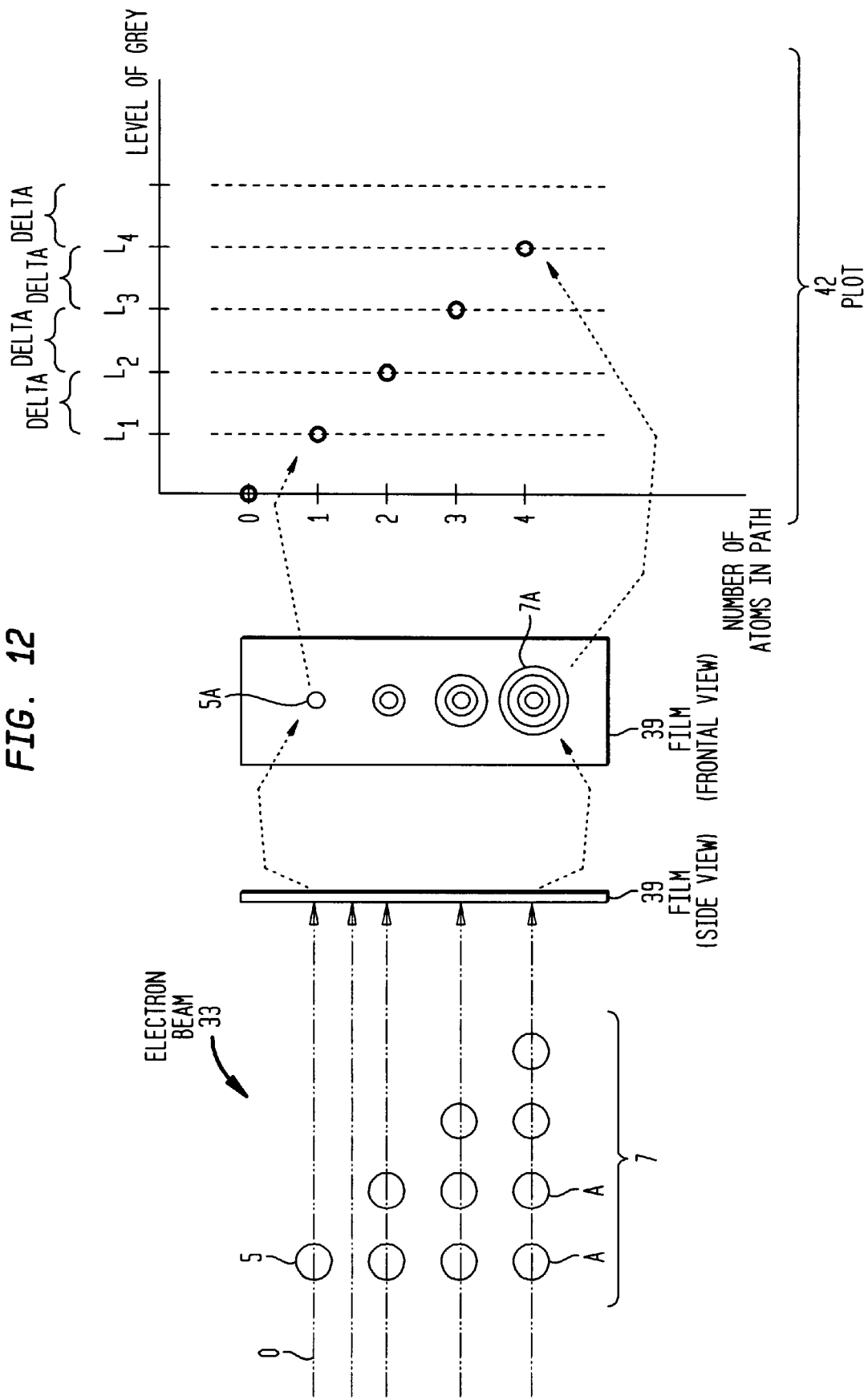

METHOD AND APPARATUS FOR DISCRETE TOMOGRAPHY

Priority benefit of the Aug. 22, 1997 filing date of Provisional Application Serial No. 60/056,931 is hereby claimed.

BACKGROUND OF THE INVENTION

1. Technical Field

The present invention relates to the field of tomography and, in particular, to the reconstruction of images from emission tomography of microscopic samples, for example, as applied to the internal structure of semiconductors. A non-linear programming algorithm, known as the expectation/maximization (EM) algorithm, is bounded and applied to the solution of the data recovered by discrete emission tomography to reproduce an image for display.

2. Description of the Relevant Art

U.S. Pat. No. 5,659,175, to Fishburn et al. describes apparatus and a method for tomography of microscopic samples. For example, let S be a finite subset of a lattice Z and let $\mathcal{L}$ be a finite collection of subsets of Z. For each $L \in \mathcal{L}$, let v(L) be the number of points in L∩S. Fishburn et al. recognized that the integer programming problem could be translated into a problem involving fuzzy sets that can be solved using linear programming. The problem of reconstructing the set S from knowledge of {v(L); $L \in \mathcal{L}$} when $\mathcal{L}$ is a collection of lines in Z in the main directions (the subject of discrete tomography and lines in main directions will be further described herein) is also considered. The approach in the '175 patent is based on (a) relaxing the constraint that S be a set to requiring that S be a fuzzy set, and (b) using a linear program to find a feasible fuzzy set. From a practical point of view (a) amounts to replacing $$v(L) = \sum_{z \in Z} X_S(z) X_L(z), \quad L \in \mathcal{L} \tag{1.1}$$

where $X_A$ denotes the indicator function of a set A, with $$v(L) = \sum_{z \in Z} f(z) X_L(z), \quad L \in \mathcal{L}, \quad 0 \le f(z) \le 1, \quad z \in Z \tag{1.2}$$

and (b) amounts to finding a feasible solution in f(z), z∈Z, for the constrained linear system (ii), using linear programming. The approach has important scientific applications in high-resolution electron-microscopy of crystals.

The problem of reconstructing an image for display from probabilities of occupancy of individual lattice sites within a crystal is described by the '175 patent in some detail, but some of the discussion is repeated here with reference to FIGS. 7–14 which correspond to FIGS. 1–7 and 13 of the '175 patent. In tomographic radiography, projection radiography is done to capture the amount of attenuation of a beam as it passes through an object as a black level but repeated many times. The repetitions produce a collection of data which is used to generate an image of the cross section of an object. That is, multiple "side views" of the object are used to generate a cross sectional view called a phantom.

Referring first to FIG. 7, some of the basic principles of tomography will be briefly described. The object "3" under scan of FIG. 7A is conceptually divided into pixels P, as in FIG. 7B. Each ray R of radiation passing through the body of object "3" is attenuated by the sequence of pixels through which it passes according to the attenuation coefficient of each pixel, unknown in real-life except when the imaged object is an experimental "phantom". A collection of parallel rays, spanning from point C to point D, produces one of the projection images. The amount of attenuation of each ray is measured using a detector for producing a numerical output. Then, an equation is derived for each ray. A simplified example is given by FIG. 7C.

If the initial intensity of the ray is $I_o$, and if the intensity of the ray after passing through the object is $I_f$ then Equation (1) is obtained for FIG. 7C:

$$I_f = [I_o e^{-\alpha_1 L_1}][e^{-\alpha_2 L_2}][e^{-\alpha_3 L_3}] \tag{1}$$

Each bracketed term in equation (1) corresponds to a position indicated in FIG. 7C.

Equation (1) results from a single ray. Since multiple rays produce each image, multiple equations are obtained for each image. Further, since numerous images are obtained, numerous sets of equations, each containing multiple equations, are obtained.

The numerous sets, of multiple equations each, are solved for the attenuation variables $\alpha$, three of which are found in Equation (1). Each $\alpha$ represents the attenuation coefficient of a pixel.

After a solution is obtained, the resulting attenuation variable, $\alpha$, for each pixel is mapped graphically, for example, by using darker colors for larger coefficients and lighter colors for smaller coefficients. The map obtained from this process is commonly called a reconstruction phantom. Since the attenuation coefficient of each pixel can be correlated with other physical parameters associated with the pixel, such as density (mass per unit volume), the mapping indicates the density pattern (or other parameter) within the phantom.

This type of tomography is called "continuous domain," because values of the attenuation coefficients in the pixels are continuous, and pixelization can be made infinitesimally fine. Discrete domain tomography relates to ascertaining the presence or absence of objects by a single binary variable when the objects may be smaller than the beam irradiating them. Briefly, and according to the '175 patent, line counts are obtained from the crystal lattice under radiation representing the number of atoms in a specific row or line. A system of equations is derived from the line counts as described by the '175 patent and a solution obtained. Referring to FIG. 13A, the count of atoms in column C1 (which is a line) is five. The line count of five produces the equation:

$$X_{11} + X_{21} + X_{31} + X_{41} + X_{51} + X_{61} = \text{line count} = 5$$

In the equations, a value of "1" for an "X" indicates the presence of an atom and a value of "0" represents the absence. Then, a system of multiple equations is obtained from the multiple line counts that are solved by linear programming processes according to the '175 patent.

Detailed procedures for obtaining line counts are known in the art. One procedure is described in "Mapping Projected Potential, Interfacial Roughness, and Composition in General Crystalline Solids by Quantitative Electron Microscopy," by P. Schwander et al., *Phys. Rev. Lett.*, 71, pp 4150–4153 (1993).

Referring to FIG. 8, a small sample 30 of a crystal is positioned in an electron beam 33 output by a transmission electron microscope, TEM. A detector detects the beam, and one can make inferences of physical features of the sample 30. The Sample 30 of the '175 patent measured approximately 100 by 100 atoms in cross section. Larger samples in cross section, for example, 1000 atoms by 1000 atoms, and three dimensional samples, for example, slices of crystals of a size 25×1000×1000 atoms can also be analyzed. An expander 36 expands beam 33. A detector 39 is, for example, a photographic film. The distance D is measurable by the human eye. When the beam 33 passes through an atom 5, a relatively faint spot is produced on film 39. When the beam passes through four atoms, the spot density may be intermediate in intensity, and so on. A ray 6 may encounter no atoms and produces no darkening. The gray levels of all spots are quantified and plotted producing a plot 42 (FIG. 12). The electron beam 33 is moved horizontally across the sample at radius R per FIG. 9.

The plot 42 can be made linear (although discrete) and of the form: y=mx+b, where y is the number of atoms, x is the grey scale value, m is the slope of a line (Delta) and b is the y-intercept. Correlations between grey scale level and number of atoms in a column are used in performing tomography on sample 30. Complex patterns can be found as in FIG. 11 and linear plots formed as in FIG. 12 or the sample may be rotated as in FIG. 10 all to the result that linear programming processes may be mathematically applied to the detected line count data to obtain a reconstruction of the illuminated object 30. For example, as between FIG. 13A and 13B the sample may be rotated 90 degrees, FIG. 13B showing the new position. The data from FIG. 13 allows a set of equations to be derived as described by the '175 patent where each x of a matrix set of equations shows the absence or presence of atoms. The constraint that is applied is that the variables "x" are limited to between 0 and 1. The '175 patent shows three reconstructed "phantoms" FIGS. 9B, 10B and 11B from simulated cross sections FIGS. 9A, 10A and 11A which may be compared with the results of applying the non-linear programming algorithm of the present invention shown in FIGS. 1–6.

SUMMARY OF THE INVENTION

The present invention applies an Expectation/Maximization algorthm (EM) processes to improve the reconstruction of images from high resolution electron microscopes. According to the principles of the present invention, a method of obtaining probabilities of occupancy of lattice sites in a sample comprises the steps of obtaining line count data and obtaining the probabilities of occupancy of the lattice sites from the line count data by non-linear programming processes, in particular, by applying the expectation/maximization algorithm bounded by the upper bound constraint that each variable is valued at less than or equal to one. The application of the non-linear programming process can obtain a phantom in 30,000 or fewer iterations and in real time (less than 4 seconds) of the EM algorithm for the exemplary phantoms of the '175 patent.

Apparatus for discrete tomography comprises a means for irradiating a sample, means for producing line count data of atoms of the irradiated sample and means for deriving a tomographic phantom from the line count data comprising a processor for applying a non-linear programming algorithm to the line count data to obtain probabilities of occupancy of lattice sites in the sample.

Further advantages and features of the present invention will be understood from the following detailed description of the present invention.

BRIEF DESCRIPTION OF THE DRAWINGS

FIGS. 1–6 show the results of the present invention, the application of a non-linear programming algorithm known as the expectation/maximization algorithm to reconstruct three discrete tomographic phantoms.

FIG. 12 shows attenuation of beams;

DETAILED DESCRIPTION

The inventors have published an article entitled "The Discrete Radon Transform and its Approximate Inversion via the EM Algorithm" International Journal of Imaging Systems and Technology, Vol. 9, pp. 155–173 (1998), which describes the present invention in some detail. The described algorithm is different from the application of the expectation/maximization algorithm discussed in an article entitled "From Image Deblurring to Optimal Investments: Maximum Likelihood Solutions for Positive Inverse problems" The Journal of the Royal Statistics Society, 55, No. 3, pp. 569–612 (1993), which generally described maximum likelihood solutions for positive linear inverse problems (LININPOS problems) in the fields of image deblurring to optimum stock selection, and an algorithm commonly used in emission tomography due to the imposition of an additional upper bound constraint on each variable $f(z)$ such that $f(z)$ is less than or equal to 1. This constraint leads to a new EM algorithm for constrained LININPOS problems which is discussed herein.

Figure 7A:
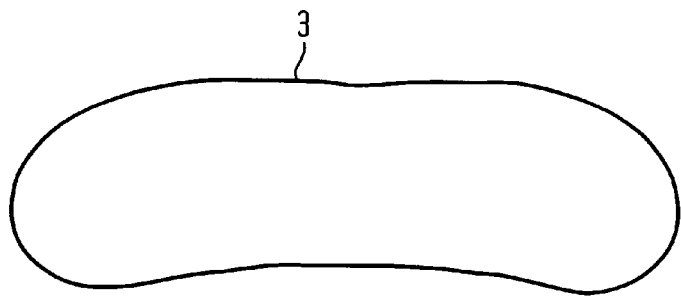
FIG. 7 illustrates the principles of tomography.
Figure 7B:
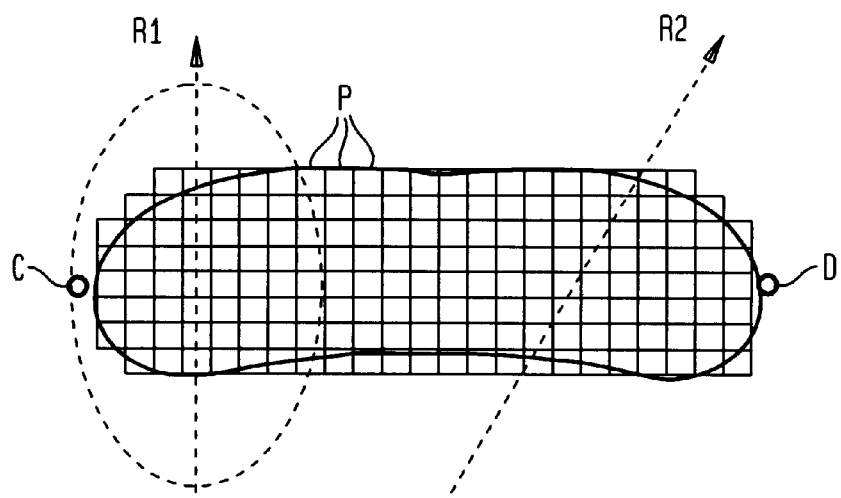
Figure 7C:
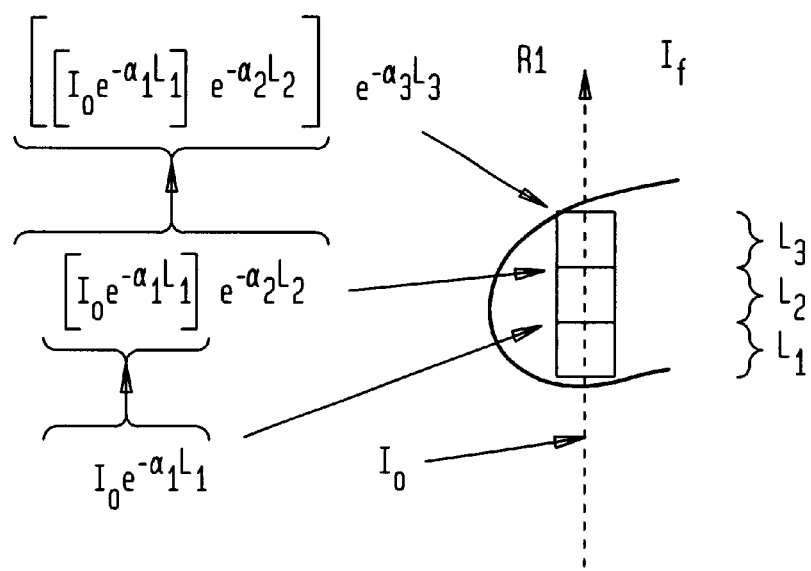
Figure 8:
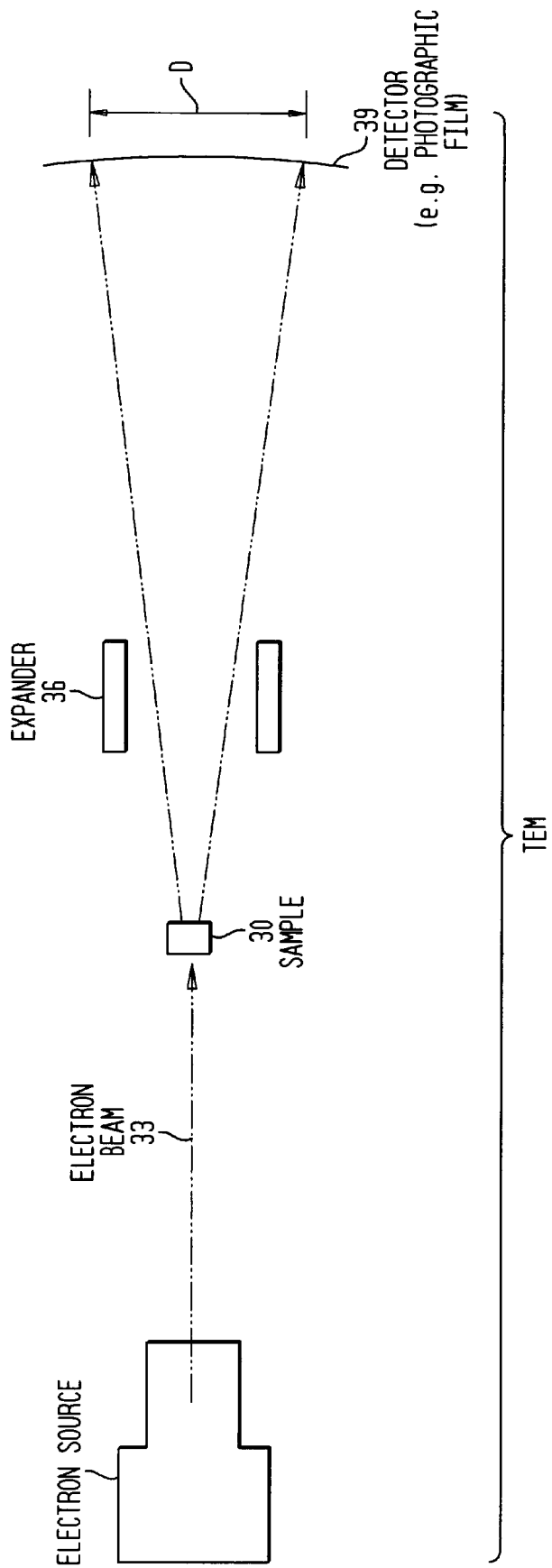
FIG. 8 illustrates use of a transmission electron microscope, TEM, to obtain line counts from a sample 30.
Figure 9:
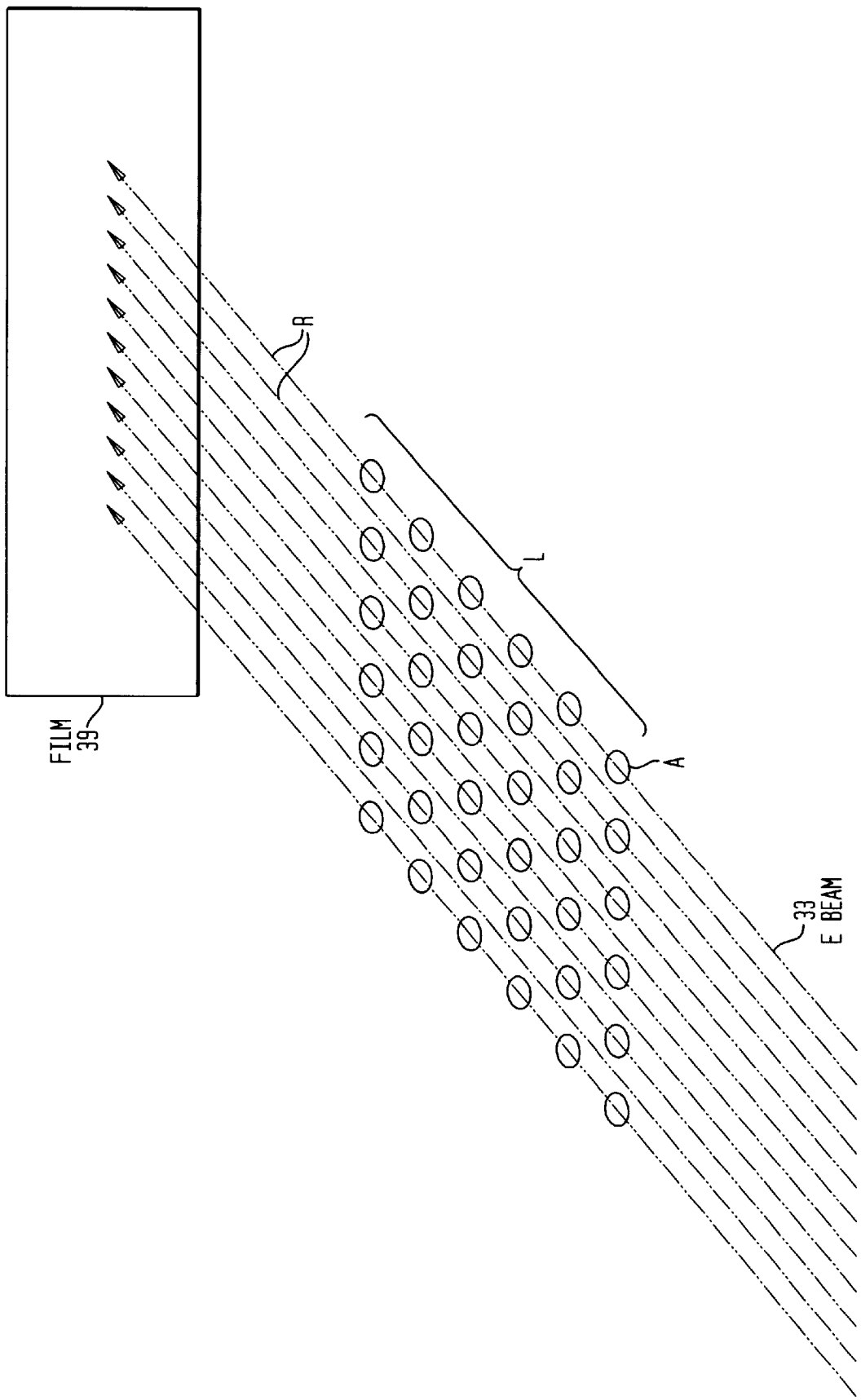
FIG. 9 illustrates passage of a beam 33 of FIG. 8 through a 6×6 lattice of atoms en route to a detector 39.
Figure 10:
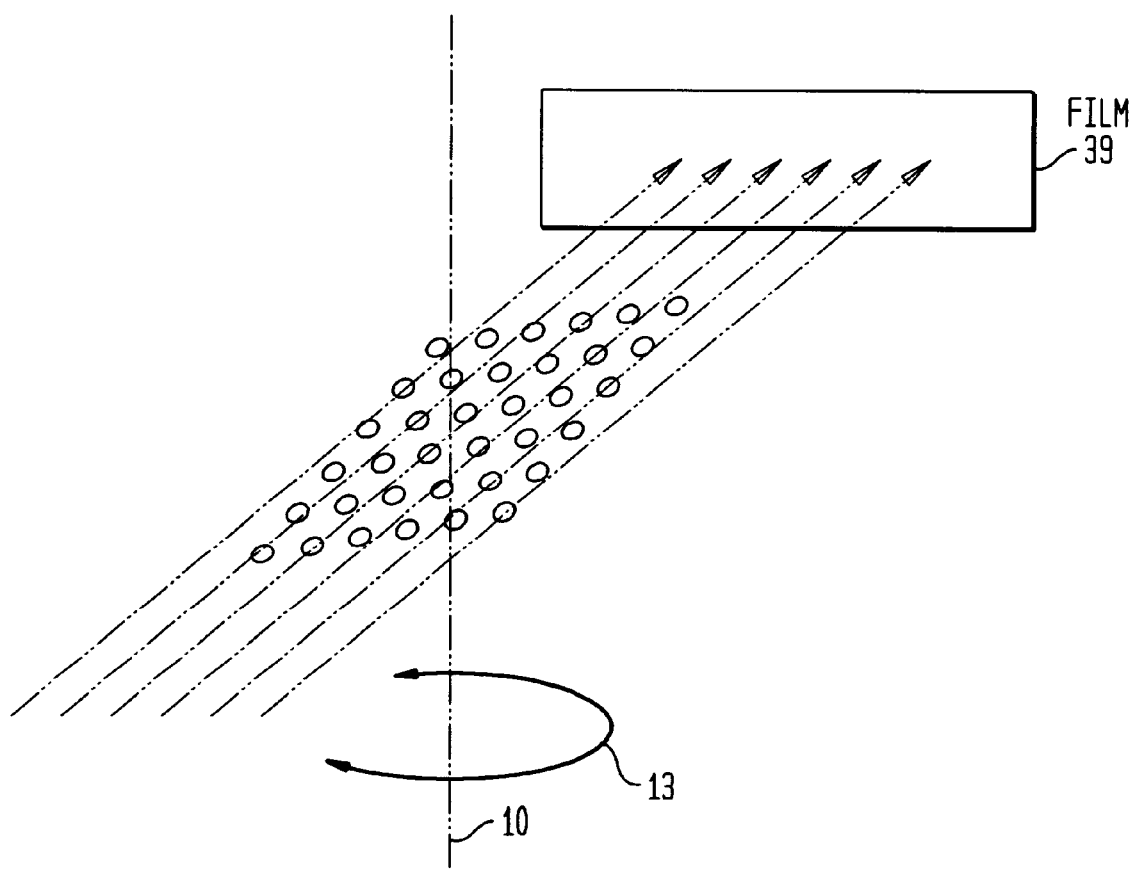
FIG. 10 shows the lattice of FIG. 9 skewed to show that a beam may pass through a sample in more than one line.
Figure 11:
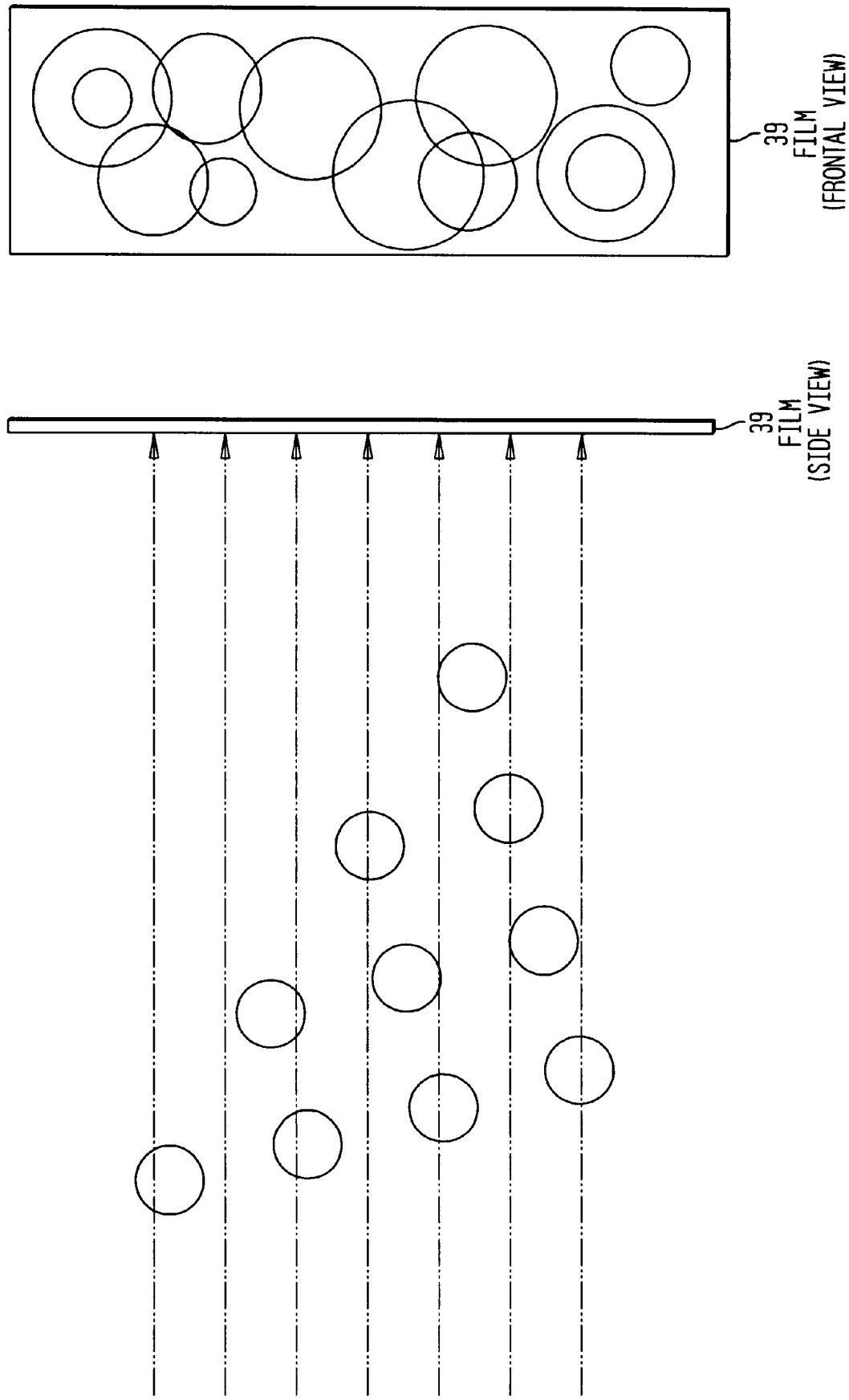
FIG. 11 illustrates a simple film result.
Figure 13C:
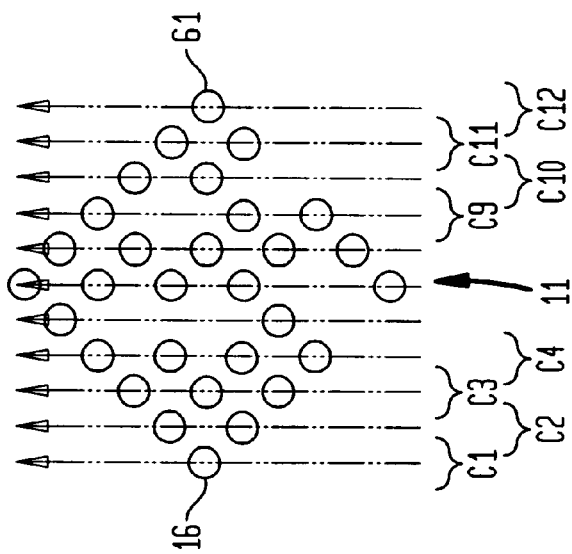
FIG. 13 show line count data collection.
Figure 13B:
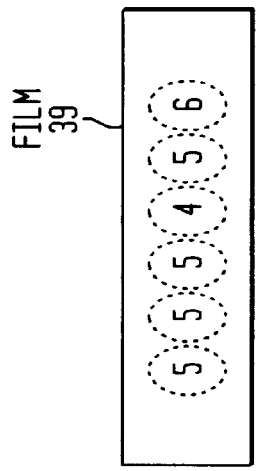
Figure 13A:
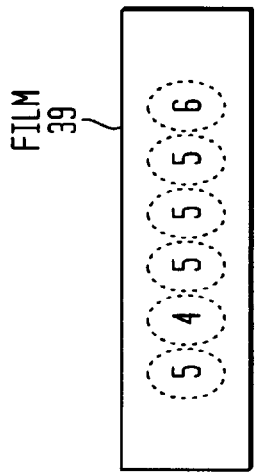
Figure 14:
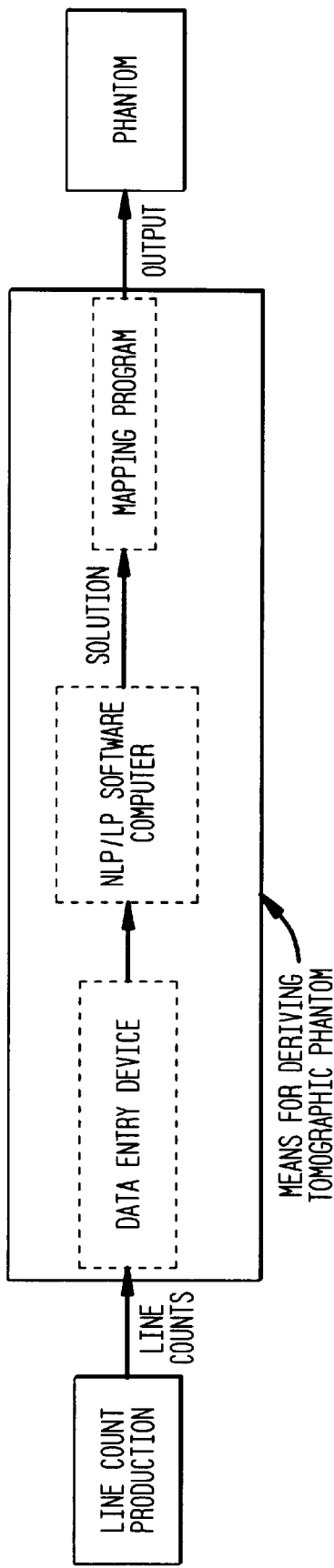
FIG. 14 shows a functional block diagram of apparatus employing processes of the present invention to obtain reconstructed phantoms.

First, the invention will be generally described followed by a more detailed discussion. FIG. 14 illustrates an apparatus employing the processes of the present invention. There is a line count production device, typically an emission tomography device such as a transmission electron microscope, a means for deriving a tomographic phantom, typically a computer processor running an algorithm and the output is data for generating a display of a phantom. The means for deriving a tomographic phantom comprises a data entry device, a linear programming software computer (in the present invention, a non-linear programming software computer) and a solution is provided to a mapping program.

The method of the present invention will noe be briefly described. First, let z denote a postion on the grid Z, representing the atomic structure of the crystal, and let $f(z)$ be equal to one or zero depending on whether in postion z of the grid Z there is an atom or not, respectively. As mentioned earlier, the high resolution electron microscope "observes" the projected values of $f(z)$ along rows (in the broad sense, including columns, diagonal, etc.) in the grid Z. This suggests equation (1.2) as a mathematical fromualtion for the problem of recovering the atomic-structure of the crystal, with the consraint on f being $f(z)=0$ or 1.

The invention presents a new approach and a novel algorithm for solving equation (1.2). Several key ingredients to the new approach are as follows. First, the binary constaint of $f(z)=0$ or 1 is replaced by the continuous or interval constraint $0 \leq f(z) \leq 1$, with the understanding that any solution for which $f(z)$ is not equal to zero or one, the solution will be post-processed, for example, through thresholding or Bayes model, and be fitted with such a solution. Second, a solution to equation (1.2) will be obtained through a minimum-distance approach. This approach entails finding an f which minimizes the distance between the left and the right sides of the equation (1.2), subject to the constraint 0<f<1. This raises the question of what is the distance function which is appropriate here, and the present invention focuses on the so-called "Kullback-Leibler information divergence index" as the "distance" function. This approach has been shown to be very effective for problems of this kind which do not have the upper-bound constraint ($f(z) \leq 1$) but only the lower-bound consraint of non-negativity ($0 \leq f(z)$). Third, the Kullback-Leibler information divergence index is a mathematical object designed to meausre the discrepency between two probability vectors, say $a=(a_1, \ldots, a_I)$ and $b=(b_1, \ldots, b_I)$ where $0 \leq b_i$, $a_i \leq 1$ and $1 = \Sigma_i a_i = \Sigma_i b_i$. If a is identical to b, the Kullback-Leibler distance between a and b, KL(a,b), is zero and vice versa whem KL(a,b)=0, the necessarily a=b. If the numerical difference between $a_i$ and $b_i$ is small (across all coordinates i) their Kullback-Leibler distance is also small.

In equation (1.2), neither the left nor the right sides of the equation are probability vectors, and so the first technical step is to rescale the problem to be probability vectors. This resealing transforms equation (1.2) into equation (2.1), shown below, plus the constraint $0 \leq f \leq b$, for some suitable value of b. Equation (2.1) without the upper-bound constraint on f, i.e., $f \leq b$, can, in principle, be solved using an EM algorithm. This is a statistical methodology designed to find the minimum KL-distance estimator (equivalent to a Maximum-Likelihood estimator). However, an EM algorithm for such problems, involving the upper bound $f \leq b$ has never been developed. The present invention develops such an algorithm. The details are shown below. This algorithm can be shown to converge to the minimum KL-distance solution.

As described above, the first step of the process is to rescale the problem of obtaining an equation set $g_j$.

An EM algorithm for constrained LININPOS problems will now be discussed. The first important observation to note is that, without loss of generality, equation (1.2) above is of the form $$g_j = \sum_{i \in I} f_i h_{ij}, \quad j \in J$$

where I and J are (finite) index sets; $g_j$'s are known, positive, and satisfy $$1 = \sum_{j \in J} g_j$$

$h_{ij}$'s are known, nonnegative, and satisfy $$1 = \sum_{j \in J} h_{ij}, \quad i \in I$$

and the $f_i$'s are unknown variables and satisfy $$1 = \sum_{i \in I} f_i$$

and $0 \leq f_i \leq b_i$, $i \in I$, for some positive constants $b_i$, $i \in I$. Thus, equation (1.2) can be substituted with the following constrained LININPOS problem:

Solve $$g_j = \sum_{i \in I} f_i h_{ij}, \quad j \in J \tag{2.1}$$

subject to the constraints:

$$1 = \sum_{i \in I} f_i, \quad 0 \leq f_i \leq b_i, \quad i \in I,$$

where $$0 \leq g_j, 0 \leq h_{ij}, i \in I, j \in J$$

and $$1 = \sum_{j \in J} g_j = \sum_{j \in J} h_{ij}, \quad i \in I$$

The transition from equation (1.2) to equation (2.1) (and conversely) is made through the following correspondences $$L \Leftrightarrow j, \quad \mathcal{L} \Leftrightarrow J; \quad z \Leftrightarrow i, \quad Z \Leftrightarrow I$$

$$g_j = v(L) / \sum_{L \in \varphi} v(L), f_i = f(z) \sum_{L \in \varphi} \chi_L(z) / \sum_{L \in \varphi} v(L) = b_i f(z) \tag{2.2}$$

$$h_{ij} = \chi_L(z) / \sum_{L \in \varphi} \chi_L(z) \equiv \chi_j(i) / \sum_{j \in J} \chi_j(i),$$

$$b_i = \sum_{L \in \varphi} \chi_L(z) / \sum_{L \in \varphi} v(L) \equiv \sum_{j \in J} v(j).$$

This is demonstrated by the following example.

EXAMPLE

Let S be the two dimensional set depicted in Display 1 below, where L represents Display 1:

|   | 1 | 2 | 3 | 4 | 5 |   |
|---|---|---|---|---|---|---|
| 1 | x | x | x | o | o | → L = 1 v(L) = 3 |
| 2 | x | x | o | o | x | → L = 2 v(L) = 3 |
| 3 | x | o | x | o | o | → L = 3 v(L) = 2 |
| 4 | o | x | x | x | x | → L = 4 v(L) = 4 |
|   | ↓ | ↓ | ↓ | ↓ | ↓ |   |
|   | L = 5 | L = 6 | L = 7 | L = 8 | L = 9 |   |
|   | v(L) = 3 | v(L) = 3 | v(L) = 3 | v(L) = 1 | v(L) = 2 |   |

Display 1: $x \in S$ $o \notin S$. Note that a matrix indexing convention is used for labeling the points on the grid.

Let $\mathcal{L}$ be the set of nine main-direction lines L. For this example, in equation (2.1)

$$g=(g_1, \ldots, g_9)=(1/24)(3,3,2,4,3,3,3,1,2).$$

The index set I is better left as double subscript, so that $i=(i_1, i_2)$ $$f=(f_{11}, \ldots, f_{15}, f_{21}, \ldots, f_{25}, \ldots, f_{41}, \ldots, f_{45}),$$

$$b=(1/24)(2, \ldots, 2, 2, \ldots, 2, \ldots, 2, \ldots, 2)$$

Note that $b_{i_1, i_2}$ = # of lines L's through the point $(i_1, i_2)$ divided by the sum of line-sums, $$\sum_{L \in \varphi} v(L)$$

This results in $b_i = 1/\#(S) = 1/12$. The fact that $b_i = 1/\#(S)$ is standard in discrete tomography where the number of line-sums through a point in S is fixed, and so $b_i$ is independent of i.

The matrix $H = \{h_{ij}\}$ is of dimension 20 (points)×9 (lines) with $$h_{ij} = h_{i_1 i_2, j} = \begin{cases} \dfrac{1}{\# \text{ of lines in } J \text{ covering } (i_1, i_2)}, & \text{if } | j \ni (i_1, i_2), \\ 0, & \text{if } | j \ni (i_1, i_2), \end{cases}$$

$$= \begin{cases} \dfrac{1}{2}, & \text{if } | j \ni (i_1, i_2), \\ 0, & \text{if } | j \ni (i_1, 2) \end{cases}$$

In summary, equation (2.1) becomes the following $$3/24 = (\frac{1}{2})(f_{11} + \ldots f_{15})$$

$$3/24 = (\frac{1}{2})(f_{21} + \ldots f_{25})$$

$$2/24 = (\frac{1}{2})(f_{31} + \ldots f_{35})$$

$$4/24 = (\frac{1}{2})(f_{41} + \ldots f_{45})$$

$$3/24 = (\frac{1}{2})(f_{11} + \ldots f_{41})$$

$$3/24 = (\frac{1}{2})(f_{12} + \ldots f_{42})$$

$$3/24 = (\frac{1}{2})(f_{13} + \ldots f_{43})$$

$$1/24 = (\frac{1}{2})(f_{14} + \ldots f_{44})$$

$$2/24 = (\frac{1}{2})(f_{15} + \ldots f_{45})$$

subject to the constraint $0 \leq f \leq (1/12)(1, \ldots, 1)$.

The Kullback-Leibler Criterion will now be described.

A simple and very useful approach for "solving" equation (2.1) is to minimize, with respect to f, the Kullback-Leibler information divergence 'distance' between g and fH, subject to the constraint $0 \leq f \leq b$. Let f be such a minimizer (always exists). Then if the linear system equation (2.1) has a solution, the minimizer k is necessarily such a solution. If equation (2.1) does not have a solution, then i has a very nice interpretation as the closest approximation to a solution in the sense of maximum likelihood. This may seem a bit artificial as there is no probability model to speak of Nevertheless, it does make sense, because of the scaling in equation (2.1) which makes g, f and the $h_{ij}$'s (fixed i) all probability functions. This guarantees that the problem of reconstructing S, or solving for f, has a genuine interpretation as a statistical estimation problem. Specifically, a simple statistical estimation problem (with data and model parameters) is constructed below for which the maximum likelihood estimate (MLE) is argmin $(0 \leq f \leq b)$ KL(g, f H), where "KL" stands for the Kullback-Leibler information divergence function.

An Equivalent Statistical Problem will now be discussed.

The model: Let (X, Y) be a random vector on I×J with the joint probability law $$P(X=I, Y=j) = f_i h_{ij}, (I, j) \in I \times J \quad (2.4)$$

where $f_i$'s and $h_{ij}$'s are as in equation (2.1):

$$0 \leq f_i \leq b_i, 1 = \sum_{i \in I} f_i = \sum_{i \in J} h_{ij}, 0 \leq h_{ij}, (i, j) \in I \times J \quad (2.5)$$

Note that the marginal distribution of X is f $$P(X = i) = f_i \sum_{i \in J} h_{ij} = f_i, i \in I \quad (2.6)$$

the conditional distribution of Y given X is $$P(Y=j|X=i) = h_{ij}, (i,j) \in I, \quad (2.7)$$

and the marginal distribution of Y, given (2.1), is $$P(Y = j) = \sum_{i \in I} f_i h_{ij} = g_j, j \in J \quad (2.8)$$

It is assumed that the g, H, and b are known, and that f is unknown.

The data:

Imagine now a large random sample of (X, Y)'s from the model described above. Assume that the X's are unobserved, the Y's are observed, and the empirical probability function of the Y's is g.

There are two important observations to note here. The first is of technical nature and the second is at the core of this novel approach:

(i) If any of the coordinates of g is an irrational number then g can't formally be an empirical distribution, regardless of the sample size. This, however, is a technical difficulty that can be fixed with a limiting argument. For simplicity of presentation we assume heretofore that all coordinates of g are rational number. This is certainly the case for any g arising from a discrete tomography problem, or just about any real-life problem.

(ii) The assumption that g is the empirical distribution of the Y's is natural and sensible. If we actually take a large sample of size N (say) of (X, Y)'s from the above model, and let $g_N$ be the empirical distribution of the Y's based on that sample, then e know from the strong law of large numbers and equation (2.8) that $g_N \to g$. Thus g is the population limit of the empirical distribution of the Y's, but since g is already given we can simply take it as our data, as this is the equivalent of having an infinitely large sample.

Thus g is 'data', while f and H are model-parameters.

The problem: Consider the model and data above with g being data, H and f being model parameters, H is known and f is unknown and to be estimated from the data g. Suppose further that there is additional 'side-information' in the form of known, given, upper-bound b on f: That is $0 \leq f_i \leq b_i$, $i \in I$. The problem is to derive the maximum likelihood estimate of the parameter f based on the data g, given the model parameters H and the upper-bound b on f.

The formulation, and the solution, for this MLE problem is given by $$\hat{f} = \mathop{\text{argmax}}_{0 \leq f \leq b} \sum_{j \in J} g_j \log \sum_{i \in I} f_i h_{ij} \qquad (2.9)$$

$$= \mathop{\text{argmin}}_{0 \leq f \leq b} KL(g, fH),$$

which is precisely the formulation given above.

Thus, even though the original problem has no probability structure, the very fact that it's entirely equivalent to a statistical estimation problem suggests that MLE and similar statistical techniques (e.g. Bayes estimation, etc.) are the correct approaches because these axe exactly the methods one would use for the statistical version of the problem.

An EM-algorithm for deriving equation (2.9) will now be discussed.

The statistical estimation problem of subsection 2.3 becomes a maximum likelihood estimation (MLE) problem from incomplete data, and the EM algorithm applies. After some algebra, one can show that the EM iteration formula is $$f^{(n+1)} = \mathop{\text{argmax}}_{0 \leq p \leq b} \sum_{i \in I} P[X = i | g, H, f^{(n)}] \log p_i, \qquad (2.10)$$

$$= \mathop{\text{argmax}}_{0 \leq p \leq b} \sum_{i \in I} f_i^{(n+1/2)} \log p_i,$$

where we define $$f_i^{(n+\frac{1}{2})} = P[\chi = i | g, H, f^{(n)}] \qquad (2.11)$$

A standard application of Bayes rule to the multinomial model implicit in equations (2.4)–(2.7) shows that $$f_i^{(n+1)} = P[\chi = i | g, H, f^{(n)}]$$

$$= f_i^{(n)} \sum_{j \in J} h_{ij} \frac{g_j}{\sum_{i \in I} f_{i'} h'_{ij}}$$

which constitutes the estimation of "E-step" of the EM-algorithm. (Note that this is similarly the iteration step of the 'standard' EM algorithm for emission tomography. The maximization or "M-step" is given by the constrained maximization problem on the right-most side of equation (2.10).

The steps of the derived EM algorithm are summarized below:

(a) Initialize with an arbitrary, but strictly positive, probability function:

$$0 < f_i^{(0)}, i \in I, \sum_{i \in I} f_i^{(0)} = 1$$

(b) Iterate the following "E" and "M" steps:
(2.12-Estimation)

$$f_i^{(n+1/2)} = f_i^{(n)} \sum_{j \in J} h_{ij} \frac{g_j}{\sum_{i \in I} f_{i'} h'_{ij}}, i \in I.$$

(2.12-Maximization)

$$f(n+1) = \mathop{\text{argmax}}_{0 \leq p \leq b} \sum_{i \in I} f_i^{(n+1/2)} \log p_i$$

Return to equation (2.12-Estimation) with $f^{(n+1)}$ replacing $f^{(n)}$.

Some remarks are appropriate about our algorithm thus derived:

1) The algorithm inherits the monotonicity property from the general 'EM theory'. In particular, the likelihood is monotone increasing from one iteration to the next.
2) Note that even when $f^{(n)}$ is in the feasible region, that is $0 \leq f^{(n)} \leq b$, $f^{(n+\frac{1}{2})}$ as defined in equation (2.12-Estimation) may land outside the feasible region. This is then fixed in equation (2.12-Maximization) where $f^{(n+\frac{1}{2})}$ is mapped into a point $f^{(n+1)}$ inside the feasible region [0, b].
3) In the unconstrained version of the problem (i.e., b=(1, . . . , 1), the maximization of equation (2.12-Maximization) results in $f^{(n+1)}f^{(n+\frac{1}{2})}$ which explains why the known EM algorithm for emission tomography and the unconstrained LININPOS problem has a one-step-iteration mapping.
4) For the current algorithm, equations (2.12), it is possible to show that $$\sum_{j \in J} g_j \log \sum_{i \in I} f(n) \chi_i h_{ij},$$

n=1, 2, . . . is a monotone increasing sequence, with fn∈[0,b], converging to $$f^{max}_{\in [0,b]} \sum_{j \in J} g_j \log \sum_{i \in I} f_i h_{ij}$$

It is worth pointing out here that the convergence proof is considerably more complicated for the current algorithm than for the simpler (one-step-iteration) emission-tomography algorithm, because in equations (2.12) the iterated values $f^{(n)}$ hit the boundary often, while in the simpler emission tomography algorithm, the iterated values always stay away from the boundary.

5) Others have discussed sufficient conditions for uniqueness of components of the recovered image, under binary reconstruction. It is important to note that all coordinates which are uniquely determined as zero or one will correspondingly have the correct value (zero or one) in the EM fuzzy-set reconstruction.
6) Step (2.12-Maximization) is a special case of a nonlinear knapsack problem, and of the problem of deriving the MLE of cell probabilities in a multinomial model, subject to upper and lower-bound constraints.

We give below two methods of solution for equation (2.12-Maximization).

Method 1 for solving equation (2.12-Maximization): An iterative approach Begin:

$$p_i^{old} = f_i^{(n\frac{1}{2})} i \in I \qquad (2.13-B)$$

Iterate:

$$p_i^{new} = \begin{cases} \lambda - 1 p_i^{old} & \text{if } p_i^{old} < b_i, \\ b_i & \text{if } p_i^{old} \geq b_i, \end{cases}$$

i∈I where λ is a scaling factor which guarantees summability to 1 and is given by $$\lambda = \frac{\sum_{i \in I} p_i^{old} I[p_i^{old} < b_i]}{1 - \sum_{i \in I} b_i I[p_i^{old} \geq b_i]}. \quad (2.14)$$

Stop: The algorithm terminates with an optimal solution as soon as $p^{new}=p^{old}$. When this occurs (always after a finite number of steps) set $f^{(n+1)}=p^{new}$.

Method 2 for solving equation (2.12-Maximization): Explicit formula

Order the ratios $f^{(n+½)}/b_i$, i∈I and let π(i) be the index of the i-th smallest ratio (ties broken by an arbitrary rule). Assume without loss of generality that the set I is actually {1, 2, . . . , I} (the simplicity of presentation makes up for the slight abuse of notation). Let $$R_j \equiv 1 - \sum_{i=j+1}^{I} f_{\pi(i)}^{(n+1/2)} = \sum_{i=1}^{j} f_{\pi(i)}^{(n+1/2)}, \quad (2.15\text{-R})$$

$$B_j \equiv 1 - \sum_{i=j+1}^{I} b_{\pi}(i), \; j=0, \ldots, I. \quad (2.15\text{-B})$$

Let j* be the first (smallest) index j, j∈{1, . . . , I} such that $$\frac{b_{\pi}(j+1)}{f_{\pi(j+1)}^{(n+1/2)}} \leq \frac{b_j}{R_j}. \quad (2.16)$$

Then $$f_{\pi(j)}^{(n+1)} = \begin{cases} \frac{B_j^*}{R_j^*} f_{\pi(j)}^{(n+1/2)} & \text{for } j=1, \ldots, j^*, \\ b_{\pi}(j) & \text{for } j=j^*+1, \ldots, I. \end{cases} \quad (2.17)$$

Simulation Experiments will now be discussed.

The novel algorithm was applied to the three examples of the '175 patent. Each of the three examples is made up of a 0–1 array (commonly referred to as "phantoms" in tomography jargon), and the available data for each of these are the horizontal, vertical, and diagonal line-sums: namely the row-margins, the column-margins, and the diagonal-margins (in direction (1, 1)). Almost all of Phantom 1 is uniquely determined by these line-sums, all of phantom 2 is uniquely determined by these line-sums, while phantom 3 has considerable portions of nonuniqueness. A thorough discussion of conditions under which parts of a binary-vector are uniquely determined from partial sums are given in the '175 patent. The novel algorithm, as outlined in equations (2.12)–(2.14), was applied to the three phantoms. The computer implementation is reasonably efficient and the code avoids repetitive calculations. (In the above description of the algorithm, we didn't pay attention to computational efficiency.) The algorithm converged in less than 40,000 iterations for phantom one and in less than 15,000 iterations for phantoms two and three. Referring to FIG. 14, there is shown a non-linear programming (NLP)/linear programming (LP) software computer of a discrete tomography system for deriving a tomographic phantom. CPU time for the non-linear programming software computer of FIG. 14 was 10 seconds for phantom one and about 6 seconds for phantoms two and three on a Silicon Graphics' Indigo computer, on a shared user basis.

The recovered values are displayed parallel to their respective phantoms in FIGS. 1A–1D through FIGS. 3A–3D, where we used thresholding for displaying purposes. For a recovered value, x say, we display "." (dot) if $x \leq L$, "1" if $x \geq U$, and the first decimal digit after round-off, with "o" standing for 0.1 (to avoid ambiguity) if L<x<U; L and U are predetermined lower and upper threshold values. This is done, separately, for four sets of threshold pairs (L, U)=(0.4,0.6), (0.3,0.7), (0.2,0.8) and (0.1, 0.9) for each of the three phantoms. (Note that L and U are independent of the bounds $f \leq b$, and are set after convergence on the recovered values in the original scale, where each point on the grid is between zero and one.) This results in the twelve figures that make up FIGS. 1A–1D through FIGS. 3A–3D.

Note that the threshold values (L, U) are not part of the reconstruction, but only influence the display of the recovered image. In fact, in the case of a unique solution, such as in phantom two, thresholding does not affect the display of the recovered image.

A Shortcut Algorithm and Further Comments will now be discussed. It appears that the algorithm can be fudged to cut computation time substantially, without significant sacrifice in quality of the recovered image. One method that we actually experimented with is the following.

Shortcut Algorithm (a) Set two threshold values, L and U, such that 0<L<U<l (e.g. (L, U)=(0.1, 0.9)).

(b) Start with a strictly positive probability vector $f^{(0)}$: values $0<f_i^{(0)}$, i∈I, $$\sum_{i \in I} f_i^{(0)} = 1.$$

(c) Define, as in equation (2.12-Estimation), $$f_i^{(n+\frac{1}{2})} \leftarrow f_i^{(n)} \sum_{j \in J} h_{ij} \frac{g_j}{\sum_{i' \in I} f_{i'}^{(n)} h_{i'j}}, \; i \in I.$$

(d) Update for i∈I $$f_i^{(n+1)} = \begin{cases} f_i^{(n+\frac{1}{2})} & \text{if } f_i^{(n+\frac{1}{2})} \leq b, \\ b & \text{if } f_i^{(n+\frac{1}{2})} > b. \end{cases}$$

(Recall that for discrete tomography $b=b_i=1/\#(S)$.)

(e) Repeat steps (c) and (d) for one-thousand iterations (the exact number of iterations is not really important, but it has to be large). Let $f^{old}$ denote the output of this process of one-thousand iterations, and define for i∈I $$f_i^{new} = \begin{cases} 0 & \text{if } f_i^{old} \leq bL, \\ f_i^{old} & \text{if } bL < f_i^{old} < bU, \\ b & \text{if } f_i^{old} \geq bU. \end{cases}$$

(f) For i∈I, if $f_i^{new}$=0 or b, set $f_i$=0 or b and mask that index i from all further updates of f. This is the final value of $f_i$ for this specific index i.

(g) Repeat steps (c) through (f), until final convergence, skipping updates of $f_i$'s for indices i which are masked (and hence already converged).

Note that the threshold values (L, U) are active parameters of the algorithm, not just of the display of the recovered image as before. This shortcut algorithm was applied to the three phantoms, again with four sets of threshold values (L, U)=(0.4,0.6), (0.3,0.7), (0.2,0.8), (0.1,0.9). Convergence took place in less than ten thousand iterations for phantoms one and two, and in less than twenty thousand iterations for phantom three. CPU time for each of these experiments was under one second on a Silicon Graphics' Indigo computer on a shared user basis. The recovered images are displayed in FIGS. 4A–4D through FIGS. 6A–6D. The results are qualitatively comparable to those obtained from the implementation of the exact EM algorithm (2.12)–(2.14).

There are other sensible variations of the EM algorithm that one can think of. The ill-posedness of LININPOS problems is a well known difficulty in image reconstruction from projections that give rise to a linear system of equations. Many 'regularization' schemes were proposed for this problem in the context of the EM-algorithm for emission tomography. See, for example, the discussion in our article referenced above for a further discussion. We would expect such regularization schemes to play a role in the application of the EM algorithm to discrete tomography too. Nevertheless, there are two important differences that we can see. First, because parts of the image are often uniquely determined, the standard EM algorithm zeros in on these uniquely determined components of the image. Second the constraint f≦b seems to moderate the oscillatory nature of the maximum-likelihood solution by comparison to the unconstrained problem. This however needs to be further studied.

In applications of discrete tomography with real data, one can expect measurement errors, in which case the data g will not be exactly the line-sums. In fact, it may not even be a vector of integers (see related discussion in the '175 patent). Our statistical-base approach to the problem is easily adaptable to such model variations as, to begin with, we treat g as experimental data. This, plus the easy adaptability to various Bayesian and other regularization schemes makes this statistical reconstruction method more appealing than the linear-programming based method in the '175 patent. Our experiments indicate that with an efficient code computation time of the EM algorithm should not be an obstacle for reasonable size real-data problems.

Other features and embodiments may come to the mind of one of ordinary skill in the art from reading the above detailed description. For example, other applications than to the measurement of crystaline samples in semiconductor fabrication processes may come to mind for the discrete tomographic processes of the present invention. The present invention should only be deemed to be limited by the scope of the claims that follow. All articles and United States patents referenced herein should be deemed to be incorporated by reference as to their entire contents.

What we claim is:

1. A method of obtaining probabilities of occupancy of lattice sites in a sample comprising the steps of
   obtaining line count data;
   obtaining probabilities of occupancy of the lattice sites from the line count data; and
   applying non-linear programming processes to obtain the probabilities.

2. A method of obtaining probabilities of occupancy as recited in claim 1 wherein said non-linear programming process comprises the expectation/maximization algorithm upper bounded by the constraint that each variable is valued less than or equal to 1.

3. A method as recited in claim 1 wherein said non-linear programming processes comprise the steps of
   initializing with an arbitrary, positive probability function $$0 < f_i^{(0)}, i \in I, \sum_{i \in I} f_i^{(0)} = 1$$

and iterating the following expectation and maximization steps to obtain a solution: the expectation step comprising:

$$f_i^{(n+1/2)} = f_i^{(n)} \sum_{j \in J} h_{ij} \frac{g_j}{\sum_{i \in I} f_{i'} h'_{i'j}}, i \in I.$$

and the maximization step comprising:

$$f(n+1) = \underset{0 \leq p \leq b}{\operatorname{argmax}} \sum_{i \in I} f_i^{(n+1/2)} \log p_i.$$

4. A method as recited in claim 1 wherein said non-linear processes comprise the steps of
   (a) setting two threshold values, L and U, such that 0<L<U<I (e.g. (L, U)=(0.1, 0.9)),
   (b) starting with a strictly positive probability vector $f^{(O)}$: values $0 < f_i^{(O)}$, i∈I, $$\sum_{i \in I} f_i^{(0)} = 1$$

(c) defining, as in equation (2.12-Estimation), $$f_i^{(n+\frac{1}{2})} \leftarrow f_i^{(n)} \sum_{j \in J} h_{ij} \frac{g_j}{\sum_{i' \in I} f_{i'}^{(n)} h_{i'j}}, i \in I$$

(d) updating for i∈I $$f_i^{(n+1)} = \begin{cases} f_i^{(n+\frac{1}{2})} & \text{if } f_i^{(n+\frac{1}{2})} \leq b, \\ b & \text{if } f_i^{(n+\frac{1}{2})} > b. \end{cases}$$

(e) repeating steps (c) and (d) for a plurality of iterations $$f_i^{new} = \begin{cases} 0 & \text{if } f_i^{old} \leq bL, \\ f_i^{old} & \text{if } bL < f_i^{old} < bU, \\ b & \text{if } f_i^{old} \geq bU. \end{cases}$$

(f) for i∈I, if $f_i^{new}$=0 or b, setting $f_i$=0 or b and mask that index i from all further updates of f, (g) repeating steps (c) through (f), until final convergence, skipping updates of $f_i$'s for indices i which are masked.

5. A method as recited in claim 2 wherein said non-linear processes comprise the iterative application of the expectation maximation algoithm upper bounded by the constraint that all variables are less than or equal to one.

6. A method as recited in claim 1 comprising the initial step of irradiating a cross sectional area of said sample of less than one thousand atoms by one thousand atoms.

7. A method of obtaining probabilities of occupancy of lattice sites by atoms in a material and displaying a phantom comprising the steps of:

obtaining line count data by irradiating the material and digitally recording intensity levels;

iteratively applying a non-linear programming algorithm to said line count data to obtain probabilities of occupancy of lattice sites in said material and displaying a phantom from said obtained probability data.

8. A method of obtaining probabilities and displaying a phantom as recited in claim 7 wherein said iterative non-linear programming algorithm comprises the expectation/maximization algorithm upper bounded by the constraint that each variable is valued at less than or equal to 1.

9. A method of obtaining probabilities and displaying a phantom as recited in claim 8 wherein said iterative non-linear programming algorithm comprises the steps of initializing with an arbitrary, positive probability function $$0 < f_i^{(0)}, i \in I, \sum_{i \in I} f_i^{(0)} = 1$$

and iterating the following expectation and maximization steps to obtain a solution: the expectation step comprising:

$$f_i^{(n+1/2)} = f_i^{(n)} \sum_{j \in J} h_{ij} \frac{g_j}{\sum_{i \in I} f_{i'} h'_{i'j}}, i \in I$$

and the maximization step comprising:

$$f(n+1) = \genfrac{}{}{0pt}{}{\text{argmax}}{0 \le p \le b} \sum_{i \in I} f_i^{(n+1/2)} \log p_i$$

10. A method of obtaining probabilities and displaying a phantom as recited in claim 8 wherein said iterative non-linear programming algorithm comprises the steps of (a) setting two threshold values, L and U, such that 0<L<U<I (e.g. (L, U)=(0.1, 0.9)), (b) starting with a strictly positive probability vector $f^{(0)}$: values $0 < f_i^{(0)}$, i∈I, $$\sum_{i \in I} f_i^{(0)} = 1.$$

(c) defining, as in equation (2.12-Estimation), $$f_i^{(n+\frac{1}{2})} \leftarrow f_i^{(n)} \sum_{j \in J} h_{ij} \frac{g_j}{\sum_{i' \in I} f_{i'}^{(n)} h_{i'j}}, i \in I.$$

(d) updating for i∈I $$f_i^{(n+1)} = \begin{cases} f_i^{(n+\frac{1}{2})} & \text{if } f_i^{(n+\frac{1}{2})} \le b, \\ b & \text{if } f_i^{(n+\frac{1}{2})} > b. \end{cases}$$

(e) repeating steps (c) and (d) for a plurality of iterations $$f_i^{new} = \begin{cases} 0 & \text{if } f_i^{old} \le bL, \\ f_i^{old} & \text{if } bL < f_i^{old} < bU, \\ b & \text{if } f_i^{old} \ge bU. \end{cases}$$

(f) for i∈I, if $f_i^{new}$=0 or b, setting $f_i$=0 or b and mask that index i from all further updates of f, (g) repeating steps (c) through (f), until final convergence, skipping updates of $f_i$'s for indices i which are masked.

11. A method as recited in claim 8 wherein said non-linear processes comprise the iterative application of the expectation/maximization algorithm upper bounded by the constraint that all variables are less than or equal to one.

12. A method as recited in claim 8 comprising the initial step of irradiating a cross sectional area of said material of less than one thousand atoms by one thousand atoms.

13. Tomographic apparatus comprising means for irradiating a sample;

means for producing line count data of atoms of said irradiated sample;

means for deriving a tomographic phantom from said line count data comprising processor means for applying a non-linear programming algorithm to said line count data to obtain probabilities of occupancy of lattice sites in said sample.

14. Tomographic apparatus according to claim 13 wherein said non-linear programming algorithm comprises the expectation/maximization algorithm upper bounded by the constraint that each variable is valued at less than or equal to 1.

15. Tomographic apparatus as recited in claim 13 wherein said means for irradiating a sample comprises a transmission electron microscope.

16. Tomographic apparatus as recited in claim 13 wherein said sample has an irradiated cross section of less than one thousand atoms by one thousand atoms.

* * * * *